(12) United States Patent
Clark et al.

(10) Patent No.: US 8,262,608 B2
(45) Date of Patent: Sep. 11, 2012

(54) APPLICATORS FOR MULTIPLE COMPONENT FORMULATIONS AND THE LIKE, AND METHODS OF USE THEREOF

(75) Inventors: Jeffrey G. Clark, Raleigh, NC (US); Keith R. D'Alessio, Carey, NC (US)

(73) Assignee: HyperBranch Medical Technology, Inc., Durham, NC (US)

( * ) Notice: Subject to any disclaimer, the term of this patent is extended or adjusted under 35 U.S.C. 154(b) by 30 days.

(21) Appl. No.: 12/019,996

(22) Filed: Jan. 25, 2008

(65) Prior Publication Data
US 2008/0195040 A1 Aug. 14, 2008

Related U.S. Application Data

(60) Provisional application No. 60/897,327, filed on Jan. 25, 2007, provisional application No. 60/975,960, filed on Sep. 28, 2007.

(51) Int. Cl.
*A61M 37/00* (2006.01)
(52) U.S. Cl. .......... 604/91; 604/92
(58) Field of Classification Search .......... 604/87, 604/89–92; 433/80, 82, 83, 90, 216, 217.1
See application file for complete search history.

(56) References Cited

U.S. PATENT DOCUMENTS

| | | | | |
|---|---|---|---|---|
| 2,662,535 A * | 12/1953 | Alboreo et al. | ........ | 132/311 |
| 3,326,215 A | 6/1967 | Sarnoff et al. | | |
| 4,060,082 A | 11/1977 | Lindberg et al. | | |
| 4,835,012 A * | 5/1989 | Saur | ........ | 427/266 |
| 5,171,149 A * | 12/1992 | Alpert | ........ | 433/217.1 |
| 5,585,007 A | 12/1996 | Antanavich et al. | | |
| 5,645,855 A | 7/1997 | Lorenz | | |
| 5,672,638 A * | 9/1997 | Verhoeven et al. | ........ | 523/112 |
| 5,928,611 A * | 7/1999 | Leung | ........ | 422/131 |
| 6,379,069 B1 | 4/2002 | May | | |
| 6,629,947 B1 | 10/2003 | Sahatjian et al. | | |
| 6,641,319 B2 | 11/2003 | May | | |
| 6,705,790 B2 * | 3/2004 | Quintero et al. | ........ | 401/132 |
| 6,869,242 B2 | 3/2005 | May | | |
| 2002/0022588 A1 | 2/2002 | Wilkie et al. | | |

(Continued)

FOREIGN PATENT DOCUMENTS

EP 0170526 2/1986

(Continued)

OTHER PUBLICATIONS

Partial International Search Report of PCT/US2008/052025, dated Feb. 6, 2009.

(Continued)

*Primary Examiner* — Nicholas Lucchesi
*Assistant Examiner* — Rebecca E Eisenberg
(74) *Attorney, Agent, or Firm* — Dana M. Gordon; Alan W. Steele; Foley Hoag LLP

(57) ABSTRACT

One aspect of the invention relates to an applicator system, and methods of use thereof, that can be used to house separately one or more liquids and one or more solids (e.g., components of a polymerizable hydrogel). In certain embodiments, the applicator systems are further designed to facilitate the mixing of the solids and liquids inside the applicator. In addition, in certain embodiments, the applicator systems are also designed to facilitate the application of the mixture to a surface.

3 Claims, 8 Drawing Sheets

[A]

[B]

[C]

U.S. PATENT DOCUMENTS

| | | |
|---|---|---|
| 2002/0122814 A1* | 9/2002 | Tedeschi et al. ............. 424/426 |
| 2002/0176732 A1 | 11/2002 | Quintero et al. |
| 2002/0198599 A1* | 12/2002 | Haldimann ............. 623/17.16 |
| 2004/0064102 A1 | 4/2004 | Yamada |
| 2004/0086479 A1 | 5/2004 | Grinstaff et al. |
| 2004/0116871 A1 | 6/2004 | Vincent |
| 2004/0131582 A1 | 7/2004 | Grinstaff et al. |
| 2005/0016549 A1* | 1/2005 | Banerjee et al. ............. 131/194 |
| 2005/0281883 A1 | 12/2005 | Daniloff et al. |
| 2006/0045900 A1 | 3/2006 | Richard et al. |
| 2006/0113318 A1 | 6/2006 | May et al. |
| 2007/0196454 A1 | 8/2007 | Stockman et al. |
| 2007/0253761 A1 | 11/2007 | May |
| 2007/0292195 A1 | 12/2007 | May et al. |
| 2009/0215923 A1 | 8/2009 | Carnahan et al. |
| 2010/0010473 A1 | 1/2010 | D'Alessio et al. |
| 2010/0069927 A1 | 3/2010 | Clark et al. |
| 2010/0280312 A1 | 11/2010 | D'Alessio et al. |
| 2010/0280547 A1 | 11/2010 | D'Alessio et al. |
| 2011/0044932 A1 | 2/2011 | Carnahan et al. |

FOREIGN PATENT DOCUMENTS

| | | |
|---|---|---|
| EP | 1188455 | 3/2002 |
| GB | 1469009 | 3/1977 |
| WO | WO-02/076534 | 10/2002 |
| WO | WO-03/047530 | 6/2003 |
| WO | WO-2005/009225 | 2/2005 |
| WO | WO-2005/048984 | 6/2005 |
| WO | WO-2005/103184 A1 | 11/2005 |
| WO | WO 2006/031358 A2 | 3/2006 |
| WO | WO 2006/031388 A2 | 3/2006 |
| WO | WO-2006/034128 A2 | 3/2006 |
| WO | WO-2006/060055 | 6/2006 |
| WO | WO 2007/001926 A2 | 1/2007 |
| WO | WO 2007/005249 A2 | 1/2007 |
| WO | WO-2007/127903 | 11/2007 |

OTHER PUBLICATIONS

International Search Report dated Sep. 1, 2009.

* cited by examiner

[A]

[B]

[C]

[A]　　　　　　　　　　　　　　　　　　[B]

[A]

[B]

[A]

[B]

[C]

[D]

[A]

[B]

[A]

[B]

APPLICATORS FOR MULTIPLE COMPONENT FORMULATIONS AND THE LIKE, AND METHODS OF USE THEREOF

RELATED APPLICATIONS

This application claims the benefit of priority to U.S. Provisional Patent Application Ser. No. 60/897,327, filed Jan. 25, 2007; and U.S. Provisional Patent Application Ser. No. 60/975,960, filed Sep. 28, 2007; both of which are hereby incorporated by reference in their entirety.

BACKGROUND OF THE INVENTION

A number of medically useful compositions comprise two or more ingredients that are not mixed together until shortly prior to use. In some instances, at least one of the ingredients is a solid, usually a powder, whereas at least one of the other ingredients is a liquid in which the solid ingredient is to be dissolved.

Use of a dual-ingredient composition of this kind can be accomplished with a conventional syringe by first loading one ingredient into the syringe, then adding the second ingredient, shaking the syringe or otherwise agitating the contents to achieve effective mixing, and subsequently dispensing the resulting mixture in the usual manner. This procedure, however, presents substantial shortcomings, including possible contamination and loss of sterility. For example, using a conventional syringe of the kind that is filled through a fill needle connected to the outlet orifice of the syringe, it is necessary to replace the needle after the first ingredient has been drawn into the syringe, in order to avoid possible contamination of the supply of the second ingredient. Even then it may be difficult to complete this procedure without rendering the outlet portion of the syringe non-sterile, particularly by extended contact with air.

Another technique that can be employed utilizes a syringe of generally conventional construction in which one ingredient has initially been loaded into the syringe, usually followed by a complete sterilization procedure for the external portion of the syringe. Again, however, it is often rather difficult to load the syringe with the second ingredient without affecting the sterile characteristics of the syringe. Moreover, in both of these procedures the manipulative steps on the part of the user are complex enough that some difficulty may be experienced.

Specialized dual-compartment syringes have been proposed for the administration of two-ingredient medications. For specialized syringes of this kind, reference may be made to Sarnoff et al. U.S. Pat. No. 3,326,215 (incorporated by reference); and Yamada U.S. Patent Application 2004/0064102 A1 (incorporated by reference). However, a dual compartment syringe of this kind is relatively costly and complex in construction, requiring structural members of different configuration from those used in conventional syringes. Moreover, filling a special purpose syringe of this kind can be quite difficult and creates other problems with regard to avoidance of contamination and maintenance of sterility.

In a different approach to this problem, Lindberg, R. M. et al. designed a dual-ingredient dispenser comprising two syringes joined by a releasable connecting sleeve. See Lindberg et al. U.S. Pat. No. 4,060,082 (incorporated by reference). In the Lindberg dispenser, one syringe, used for mixing and dispensing the medication, comprises a housing with inlet and outlet valve-seal members at its opposite ends, and contains a first ingredient in a mixing chamber between the valve-seal members, with the inlet valve-seal member being actuatable from closed to open condition by a fill needle; the other syringe is a carrier syringe filled with a second ingredient and equipped with a fill needle held in alignment with the inlet valve-seal member of the first syringe. Mixture of the material may be achieved by manually shaking the dispenser; however, complete mixing may not occur, especially when forming viscous compositions. In addition, dispensing of the material post-mixing requires the insertion of an additional component into the dispenser.

The known applicator systems are expensive, difficult to sterilize, and/or comprise multiple components, which makes them hard to use. Therefore, there exists a need for an applicator system which is easy to use, can be made sterile, and is inexpensive. Such applicator systems, and methods for their use, are described herein.

SUMMARY OF THE INVENTION

One aspect of the invention relates to an applicator system, and methods of use thereof, that can be used to house separately one or more liquids and one or more solids (e.g., components of a polymerizable hydrogel), is further designed to facilitate the mixing of the solids and liquids inside the applicator, and is also designed to facilitate the application of the mixture to a surface. In certain embodiments, such an applicator may be used for delivering a composition to a tissue. For example, in certain embodiments such an applicator may be used for delivering a formulation to a cornea. In addition, it is understood that these applicators may also be useful for a variety of applications including, for example, preparation and application of a vascular sealant and arterial access closures.

A further objective of the invention is to provide an applicator system for which the manipulative steps required for use are held to a minimum and/or the number of components is held to a minimum.

In certain embodiments of the invention, the applicator systems of the invention are constructed in part from conventional components and require virtually no specialized structural elements. In addition, in certain embodiments, the invention relates to applicator systems that are simple and inexpensive in construction, yet effectively minimize the aforementioned problems and difficulties of contamination, non-sterility, segregation of liquids prior to sterilization and/or use, and complete mixing of the solid and liquid portions.

In certain embodiments, a mixture of liquids is provided in a crushable ampoule (such as a glass ampoule) which can be crushed just prior to use. In an alternate embodiment, multiple liquids are provided in their own ampoules. In certain embodiments, a solid, or mixture of solids, is provided in a crushable ampoule.

In certain embodiments, two or more liquid portions are held in separate compartments, separated from each other by friable seals. In certain embodiments, the solid and liquid portions are held in separate compartments, separated from each other by friable seals. In certain embodiments, one or more of the friable seals are wax seals.

More detailed and specific aspects of the present invention will be understood by reference to the following figures and detailed description which illustrate by way of example a few of the forms of the invention within the scope of the appended claims.

DETAILED DESCRIPTION OF THE INVENTION

There is a need to develop improved dispensers that facilitate the complete mixing of solids and/or liquids inside the dispenser while maintaining the sterility of the mixture. In addition, there is need for a system for dispensers that allow two or more components which are to be mixed to be kept separate until just prior to use. Further, it would be advantageous if the dispensers could also act as applicators, thereby facilitating the application of the mixture. The present invention addresses these needs and others.

One aspect of the invention relates to an applicator system that may be used to house multiple components (e.g., components of a polymerizable hydrogel, such as solids and liquids), facilitating the mixing of the components inside the applicator, and further facilitating the application of the mixture. Another aspect of the invention relates to an applicator system that may be used to house multiple liquids and a solid (e.g., components of a polymerizable hydrogel), facilitating the mixing of the solid and liquids inside the applicator, and further facilitating the application of the mixture. Another aspect of the invention relates to an applicator system that may be used to house one liquid and one solid (e.g., components of a polymerizable hydrogel), facilitating the mixing of the solid and liquid inside the applicator, and further facilitating the application of the mixture.

While the invention will often be described herein as facilitating the formation and effective delivery of a polymerizable hydrogel formulation to a patient, this is not intended in any way to limit the scope of the invention to such an application. Rather, the applicators of the invention, and the methods of the invention, may be used in any application requiring mixing two or more components (e.g., solids and liquids) prior to use. It is understood that these applicators may also be useful for a variety of applications including, for example, preparation and application of a vascular sealant and arterial access closures.

In certain embodiments, the applicators of the invention can be used to prepare and apply a hydrogel formulation (such as a liquid ocular bandage product). In certain embodiments, the hydrogel formulation is delivered in liquid form and quickly polymerizes into a soft hydrogel. In certain embodiments, the hydrogel formulation comprises three basic components: a cross linker (such as PEI); an activated polymer (such as activated PEG); and a buffer solution.

Figure 7:
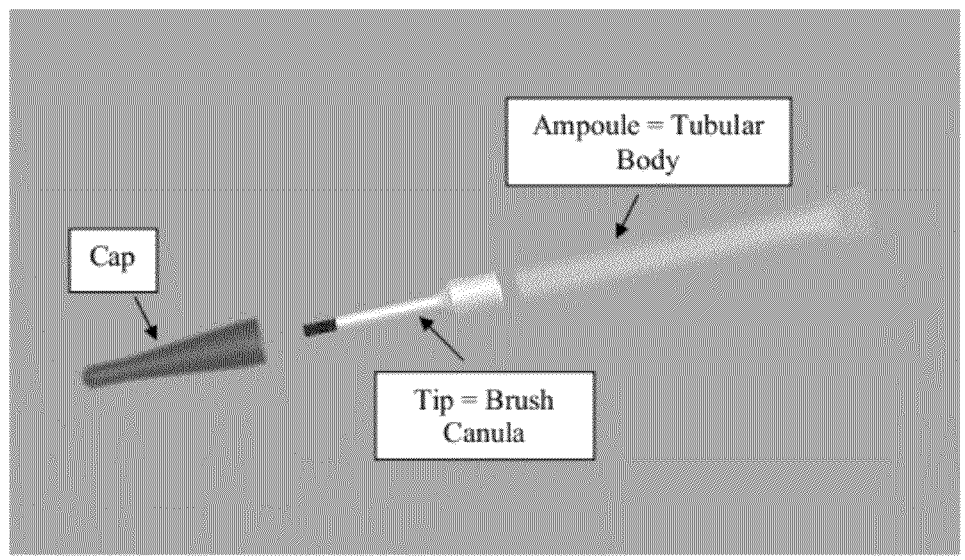
FIG. 7 depicts [A] an "exploded view" and [B] an "assembled configuration" of one type of applicator of the invention.
Figure 7:
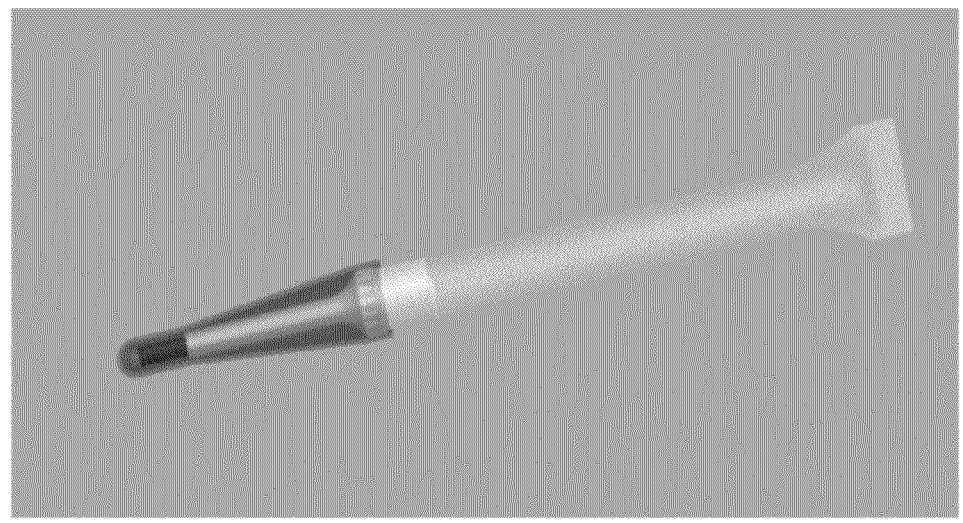
Figure 8:
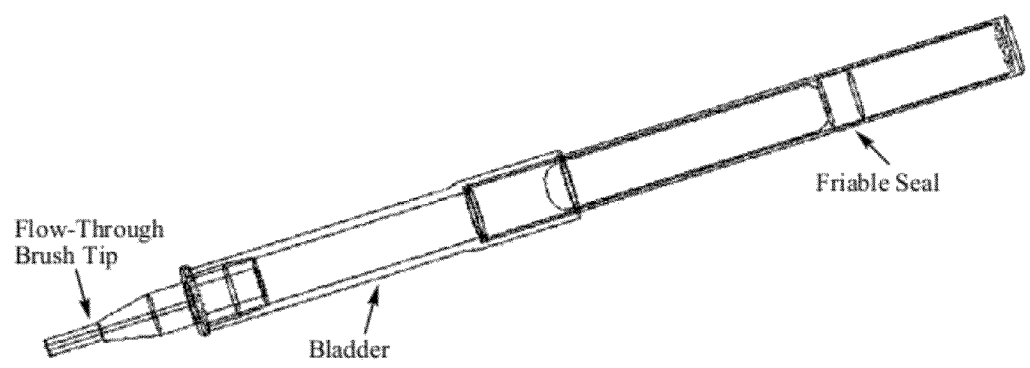
FIG. 8 depicts [A] an example of a single wax pen applicator; and [B] an example of a plastic amp-bladder applicator.
Figure 8:
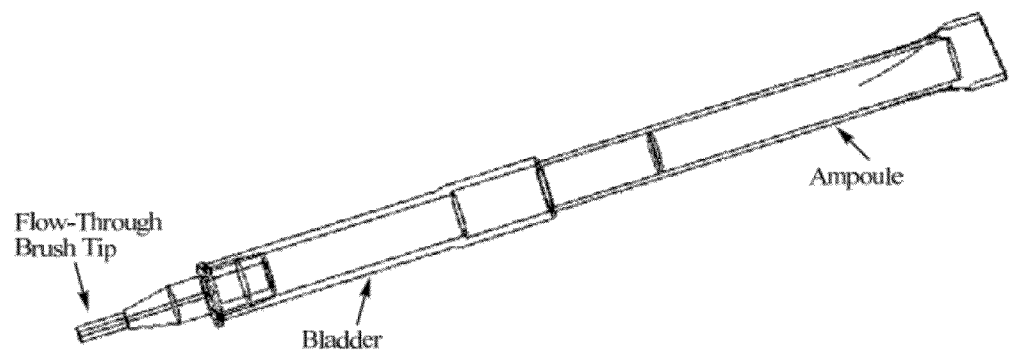

As described in more detail below, certain applicators have one storage receptacle for the liquid portion and another, separate, storage location for the powdered portion of a formulation. One such embodiment of the invention is shown in FIG. 7. FIG. 7A is an exploded view of one embodiment of the inventive applicator; FIG. 7B shows the device in its assembled configuration. In this embodiment, the applicator consists of three basic components: a cap, a tip (in this case, a brush cannula tip) and an applicator body. The brush cannula is designed with an internal orifice which allows liquid communication between the brush in the most distal portion of the applicator body and the most proximal aspect of the applicator body; it fits snugly into the distal portion of the tubular applicator body. The cap then fits snugly onto the exterior surface of either the brush cannula or directly over the tubular applicator body.

In one embodiment, the applicator body is tubular and houses the liquid portion of the polymerizable hydrogel. In this embodiment and others, the powdered portion of the polymerizable hydrogel is housed in the proximal cavity of the brush cannula. Manual pressurization of the exterior of the tube by the user forces the liquid portion into the powdered portion of the hydrogel. The cap is design to have a larger internal volume than that of the combined liquid and solid portions of the hydrogel and thus completely contains the mixed formulation within the interior of the cap. Upon cessation of the manual pressurization, the mixed hydrogel formulation will be sucked back into the tubular applicator body. Repeated pressurization and release of pressure effectively mixes the hydrogel components. At time of use, the cap is removed and gentle pressure applied to the tubular applicator body, forcing the mixed hydrogel first through the cannula, and then out through the brush, which is then used to apply a thin layer onto the appropriate tissue.

In certain embodiments, to facilitate the mixing of the components in the cap, the cap is designed to allow both for air to pass out of the cap, once a component is injected into the cap, and for air to pass into the cap, when the component is sucked back into the applicator body. An airtight cap, wherein no material can be injected into the cap, is referred to as "airlocked." Caps which allow the passage of air, as described above, are there to cover the tip in a "non-airtight" manner.

In other embodiments, the powdered portion of the hydrogel is housed within the space between the brush cannula and the interior aspect of the cap. As in the first embodiment, pressurization forces the liquid into the powder and release of pressure causes the mixed components to be sucked back into the tubular applicator body. The formulation is applied as described herein.

In certain embodiments, the release of liquid from the applicator body requires a seal to be broken. Once the seal is broken the liquid can pass from the applicator body into the solid-containing tip or cap. In certain embodiments, the cap can be used to puncture the seal. In certain embodiments, the seal is coated with a wax or a plastic to ensure no passage of liquid through the seal before it is broken.

In certain embodiments, the tip of the invention is a brush tip such as an Andon Brush Flow-Thru Brush Tip ("flow-thru brush"). An flow-thru brush is a commercially available brush applicator tip usually used with a bottle or syringe to apply liquids to surfaces. The bristles of the flow-thru brush are arranged around a central cannula such that fluid flows through the cannula, through the open center of the bristle assembly and wicks into the bristles and out onto the surface to be coated with liquid. In certain embodiments, the overall length is approximately 1 inch with an outside diameter at the shank of about 0.25 inches.

Figure 1:
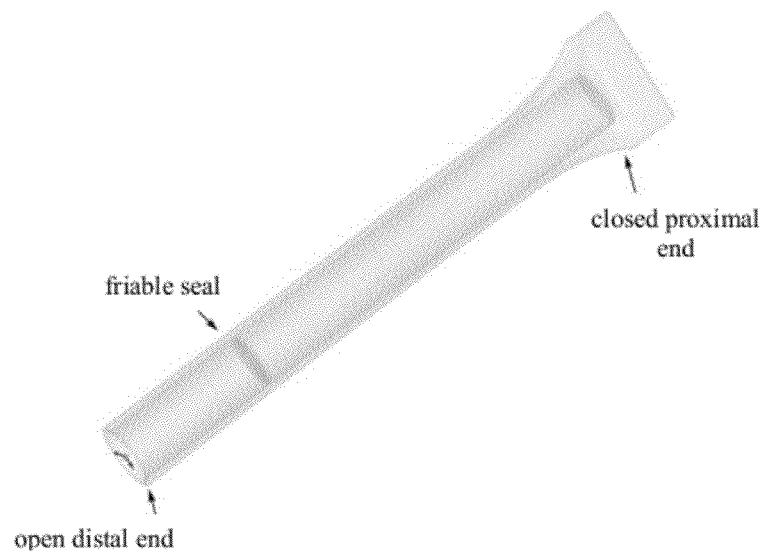
FIG. 1 depicts selected exemplary components of the invention: [A] a James Alexander Corporation Plastic Ampoule ("JAC plastic amp"); [B] a nozzle tip; and [C] an flow-thru brush tip.
Figure 1:
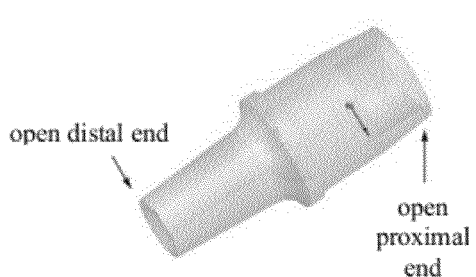
Figure 1:
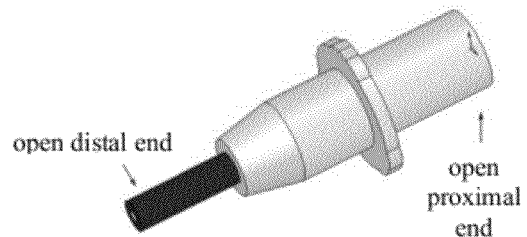

In certain embodiments, the brush cannula is replaced by a simple cannula without a brush. In certain embodiments, the tip of the invention is a James Alexander Corporation Nozzle Tip ("nozzle tip") as shown in FIG. 1B. The nozzle tip is a commercially available tip with an interior cannula which is designed to fit within the JAC Plastic Amp and direct the flow of a liquid through the device and onto a surface. It is approximately 0.320 inches in outer diameter (at shank) and 0.8 inches in overall length In other embodiments, alternative tips are used in place of the brush cannula or a simple cannula. These could include a foam swab, a porous plastic component, a duck bill tip, a textile mitt or a spray tip.

In certain embodiments, the applicator body of the invention is a James Alexander Corporation Plastic Ampoule ("JAC plastic amp") as shown in FIG. 1A. The JAC plastic amp is a plastic tubular device which has a friable seal approximately ¾ of an inch from the open distal end. It is commercially available in both polyethylene and polypropylene. The friable seal separates a closed proximal end which is filled with a liquid portion from the open distal end. The device is approximately 3 inches long and 0.350 inches in diameter with a wall thickness of about 0.020 inches. At time of use, the user pinches the tube at the friable seal, which breaks, liberating the liquid portion. Additional manual flexure of the tube pressurizes the liquid in the formerly sealed proximal end, driving it towards the open distal end.

In other embodiments, the tubular applicator body is a metallic tube. For example, a soft aluminum tube or a laminate tube, such as a glaminate tube. If needed, an additional component (referred to herein as a springing mechanism) may be added into the interior of the metallic tube in order to effect a spring back of the tube, thus facilitating the sucking back of the mixed hydrogel components into the tube.

In certain embodiments, the powdered portion is assembled within the tip/cap assembly and stored separately from the liquid filled tubular applicator body portion. This will facilitate the storage stability of the device. At time of use, the tubular applicator body and the tip/cap assembly are attached to each other, just prior to mixing of the hydrogel components.

In another embodiment, the tubular applicator body is a polymer tube in which interlocking separators prevent liquid communication between the liquid containing portion of the applicator and the powder containing portion of the applicator. At time of use, the interlocking separators are removed and mixing of the hydrogel components is allowed.

Figure 2:
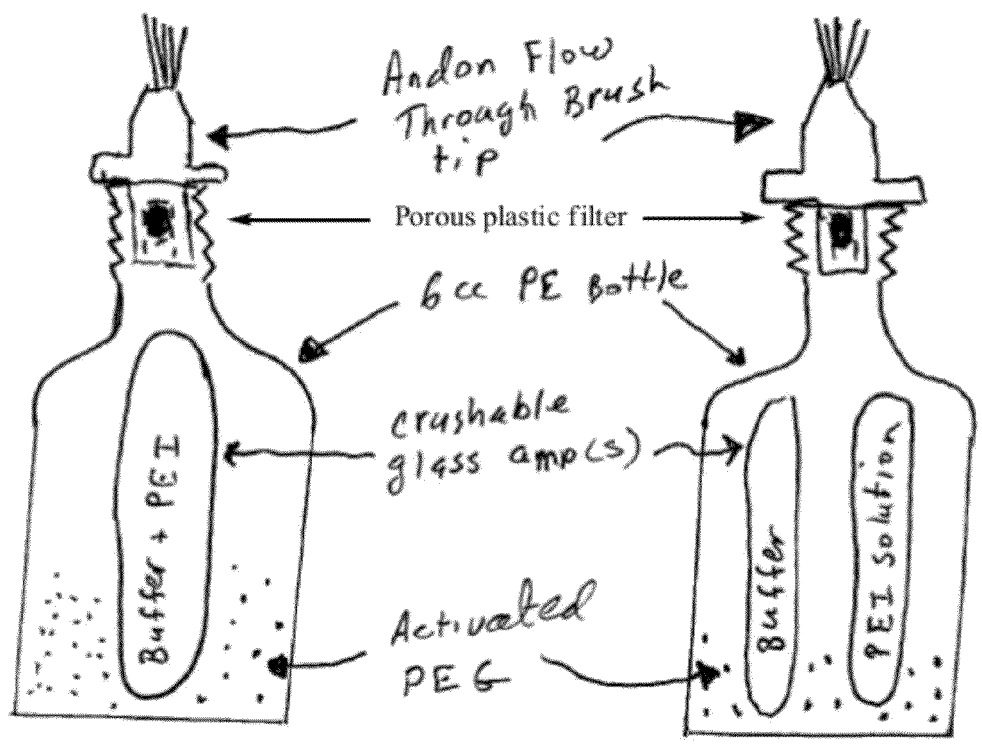
FIG. 2 depicts bottles, containing activated PEG, a flow-thru brush tip, and either [A] a single crushable ampoule filled with buffer-PEI solution (left) or [B] two separate crushable ampoules, one holding a buffer and the other holding a PEI solution.

Certain embodiments of the invention relate to additional applicators which have separate compartments for liquid portions of a formulation, as well as a separate storage location for powdered portions of the formulation. One such embodiment of the invention is shown in FIG. 2. In this embodiment, the applicator consists of the following basic components: a bottle (applicator body) which contains one or more ampoules containing liquids and solid; and a tip. The tip shown in FIG. 2 is a brush cannula tip. The brush cannula tip is designed with an internal orifice which allows liquid communication between the brush in the most distal portion of the bottle and the most proximal aspect of the bottle; it fits snugly into the distal portion of the bottle.

In one embodiment of the invention a 6 cc polyethylene bottle was fitted with either a single crushable ampoule filled with a buffer-PEI solution or two separate crushable ampoules (one with PEI-water solution and the second with buffer solution). To the open neck of the bottle, a flow-through brush applicator with a MicroPore® filter was attached.

Figure 3:
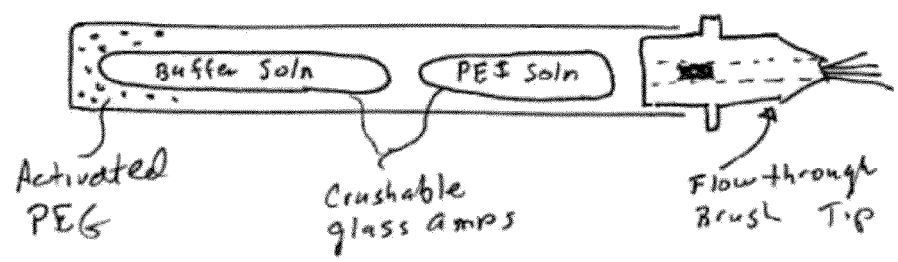
FIG. 3 depicts [A] a tandem ampoule applicator and [B] a tandem ampoule applicator with a mesh or screen.
Figure 3:
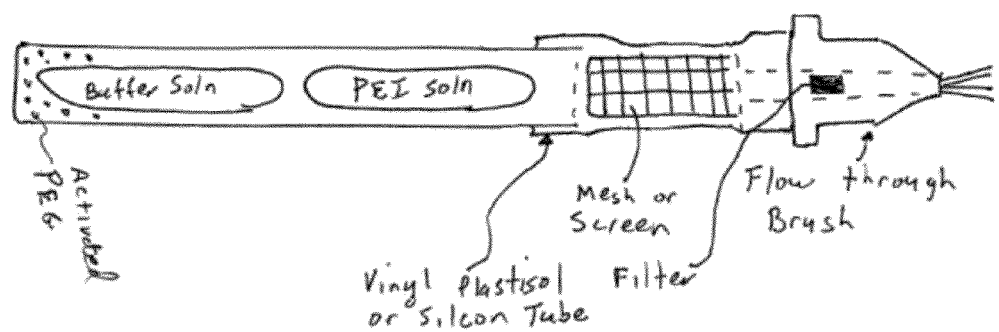

In another embodiment, a tandem ampoule applicator was conceived which would incorporate a tubular body into which activated PEG would be placed, followed by a buffer solution ampoule, then a PEI solution ampoule and finally an flow through brush tip with MicroPore® filter (see FIG. 3A). This configuration retained the benefits of separating the PEI and buffer solutions and added the advantage that the user could be definitively instructed to break the bottom ampoule first (buffer solution), mix to reconstitute the activated PEG, then break the upper ampoule (PEI solution), mix a second time and apply.

In another embodiment, a tubular applicator body containing activated PEG inside the applicator body, a buffer containing ampoule and a separate PEI solution containing ampoule both inside the tubular applicator body. In certain embodiments, a vinyl or silicon (rubber) tube is fitted to the open end of the tubular body (see FIG. 3B). A piece of screen material is added to the interior aspect of the rubber tube in order to retain the larger portions of the glass shard in the tubular applicator body. The flow-thru brush tip is then fitted to the other end of the vinyl or silicon tube. This configuration retains all of the advantages of the applicators discussed above and has the additional advantage of excluding glass shards from the area where users instinctively wish to hold and squeeze the device. This design also makes it easier to squeeze the applicator and expel the liquid formulation.

In preparing hydrogels, the chemical reaction that causes the liquid formulation to gel may be dependent upon pH. For example, when forming a PEI/PEG-SG hydrogel, the PEI solution is basic and the buffer solution is acidic such that when mixed together, the resulting liquid has the correct pH to cause the dissolve PEG-SG to polymerize and gel within a reasonable time. However, the exact local pH is dependent upon the way that the PEI ampoule has broken and the extent of mixing that occurs during the manual shaking of the device. Therefore, for certain applications, in addition to keeping the liquid portions separate prior to sterilization (as discussed above), it would be advantageous to mix completely the liquid portions prior to mixing the liquids with the solid portions (just prior to use).

In certain embodiments, the solid portion (e.g., PEG-SG) is placed into a glass ampoule. This may be an advantage over applicators which have the solid portion loose in the applicator body. For example, by placing the PEG-SG inside a glass ampoule, the PEG-SG is protected from the moisture of the environment and/or the other components of the applicator.

In certain embodiments, the tubular applicator body is utilized as a place for depositing and retaining the liquid portions of the formulation.

In certain embodiments, the applicator separately houses two liquids in chambers separated from each other by friable seals. In addition, in certain embodiments, a solid portion (such as an activated PEG powder) is housed in a crushable glass ampoule. In certain embodiments, the solid portion is separated from the liquid portions by a friable seal. In certain embodiments, one or more of the friable seals are wax. In certain embodiments, the applicator incorporates a rubber bladder attached to the distal third of the applicator body, as well as a flow through brush tip at the most distal end of the bladder. In the interior of the bladder is a screen which prevents large glass shards from entering the bladder. When using such an applicator, once the materials are completely mixed, gentle pressure on the bladder will cause the mixed formulation to flow through the brush tip for application onto a surface (such as an ocular surface).

Figure 5:
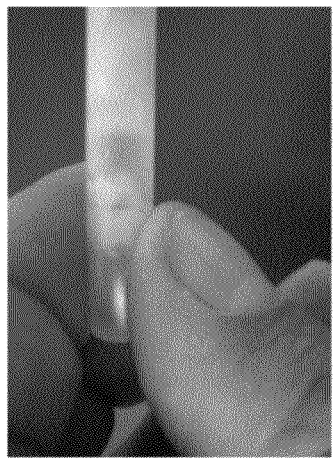
FIG. 5 depicts an approach for using an applicator (e.g., an applicator as shown in FIG. 4) of the present invention.
Figure 5:
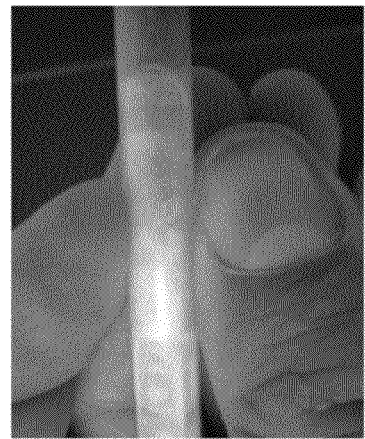
Figure 5:
Figure 5:

FIG. 5 shows one approach to the mixing and delivery of a formulation to a surface. As shown in FIG. 5A, with applicator brush tip pointed upward, the applicator body is squeezed several times at the point where the bottom friable seal resides. This force will break the friable seal and allow the two liquids to mix. This step can be done at any time prior to use without any deleterious effects. As shown in FIG. 5B, with the applicator brush tip pointed upward, the applicator body is squeezed several times where the upper friable seal resides. This force will break the upper friable seal and allow the mixed liquids to communicate with the powder filled glass ampoule. Alternatively, the upper friable seal can be broken first and the lower friable seal can be broken second. These two steps can be accomplished prior to use without any deleterious effects for several hours.

At time of use, with applicator tip pointed upward, the glass ampoule is crushed and the applicator is shaken aggressively, as shown in FIG. 5C. This action begins the dissolution of the solid and subsequent chemical reaction that forms the hydrogel. The formulation is then applied to a surface before the hydrogel forms, as shown in FIG. 5D. A gentle tapping or slight shaking motion may help facilitate the mixed liquid formulation towards the brush tip and thus facilitate expression onto the surface.

In certain embodiments, the applicator utilizes wax as a friable seal. The wax may either be delivered to the surface of the liquid in a molten form and allowed to cool to a solid or it is delivered to the surface of the liquid as a solid that is heated until melted and then allowed to cool down. In fact, most polymerizable substances that would go on the surface of the liquid and then be polymerized into a solid may be used. For example, such materials as photoinitiated polymers and moisture initiated polymers, such as cyanoacrylate, would be good candidates.

In certain embodiments, to aid in the identification of the friable seals for the purpose of providing instructions to the user, the friable seals can be different colors (e.g., red and blue). The user can be instructed to break the red seal first and the blue seal second. When the friable seals comprise wax, colored wax can be used.

In certain embodiments, when wax is used as a friable seal, the wax may comprise ferrous metal particles, or the like, admixed such that an inductive heating coil could be utilized to heat the wax to its melting point.

In certain embodiments, wax with ferrous particles could be used for the lower seal and the upper seal could remain unmodified wax. Devices of this embodiment could be made, packaged, sterilized and then subjected to an inductive heating cycle which would disrupt the lower seal allowing the buffer and PEI to mix sometime after sterilization, but well before use.

In certain embodiments, the applicator body of the invention is a plastic tubular device which has a closed proximal end and an open distal end. In certain embodiments, the applicator body is made of polyethylene or polypropylene. In certain embodiments, the applicator body is approximately 3 inches long and about 0.350 inches in diameter with a wall thickness of about 0.020 inches. At time of use, the user pinches the tube in an appropriate sequence, which breaks the ampoules and/or friable seals, liberating the solid and/or liquid portions. Additional manual flexure of the tube pressurizes the liquid in the proximal end, driving it towards the open distal end.

In other embodiments, the tubular applicator body is a metallic tube. For example, the applicator body could be made of a soft aluminum tube or a laminate tube, such as a glaminate tube. If needed, an additional component (referred to herein as a springing mechanism) may be added into the interior of the metallic tube in order to effect a spring back of the tube, thus facilitating the mixing of the hydrogel components into the tube and their subsequent expulsion from the tube.

In another embodiment, the tubular applicator body is a polymer tube in which friable seals (e.g., wax seals) prevent liquid communication between the liquid portions of the applicator. At time of use, the friable seals are broken (or melted) and mixing of the liquid portions is allowed.

In certain embodiments, a bladder may be inserted between an applicator body and a tip. For example, a PVC plastisol bladder can be attached to an Andon flow through brush and a JAC Plastic Amp. In certain embodiments, in the interior space of the brush/bladder assembly can be placed a solid (e.g. an activated PEG) and a cap was placed on the proximal end. Separately a JAC Plastic Amp can be filled with a mixed PEI/buffer solution and heat sealed. These two assemblies can be placed into separate Mylar® foil bags or into separate cavities within a single foil Mylar® pouch. At time of use, the scrub nurse or physician would remove the two assemblies, remove the cap from the back end of the brush tip/bladder assembly and fit the bladder to the open end of the JAC plastic Amp. At time of use a physician would squeeze the plastic amp to break the internal septum and squeeze the plastic amp body to get the PEI/buffer solution to flow down into the bladder. The physician then would shake to mix the liquid and powdered activated PEG and squeeze the bladder to express the mixed formulation onto the intended tissue surface.

Another aspect of the invention relates to the adsorption of a solid portion of a hydrogel onto an insoluble solid support. This solid-containing insoluble solid support may be brought into contact with a liquid, thereby forming a hydrogel. A remarkable, unexpected advantage of this approach (over the formation of a hydrogel by direct mixing of a solid and a liquid) is that by adsorbing the solid portion onto the insoluble solid support one avoids the entrapment of air upon the mixing of solid and liquid portions. This feature is of note because entrapped air can adversely effect the delivery and or quality of the hydrogel.

Another aspect of the invention relates to a hand-held brush applicator. As with the applicators described above, the hand-held brush applicator can facilitate the mixing of the solid and liquid inside the applicator and/or facilitate the application of the solid-liquid mixture. The use of an inventive hand-held brush applicator is of particular advantage in precise applications, such as the application of sealants/adhesives for ocular and vascular uses. In certain embodiments, the inventive hand-held brush applicators of the invention allow the delivery of a composition to a patient while reducing or eliminating air bubbles typically caused by such an application. In certain embodiments of the invention, the hand-held brush applicator may be used for the effective delivery of a polymerizable hydrogel formulation to a patient.

Selected Applicators

One aspect of the present invention relates to an applicator, comprising an applicator body, a tip and a cap;

wherein the applicator body comprises a storage receptacle for a liquid portion, a closed proximal end, an open distal end, and a friable seal or a removable separator separating the storage receptacle for the liquid portion from the open distal end; the tip comprises an open proximal end connected to the open distal end of the applicator body, and an open distal end; the cap covers the open distal end of the tip in a non-airtight manner; and the tip or the cap comprises a storage receptacle for a solid portion.

In certain embodiments, the present invention relates to any of the aforementioned applicators, wherein the applicator body is tubular. In certain embodiments, the present invention relates to any of the aforementioned applicators, wherein the applicator body is a plastic ampoule.

In certain embodiments, the present invention relates to any of the aforementioned applicators, wherein the applicator body further comprises a liquid in the storage receptacle for a liquid portion. In certain embodiments, the present invention relates to any of the aforementioned applicators, wherein the liquid comprises a polyalkyleneimine. In certain embodiments, the present invention relates to any of the aforementioned applicators, wherein the liquid comprises PEI.

In certain embodiments, the present invention relates to any of the aforementioned applicators, wherein the applicator body is made from a compressible material, wherein the compressible material permits manual pressurization. In certain embodiments, the present invention relates to any of the aforementioned applicators, wherein the compressible material comprises plastic. In certain embodiments, the present invention relates to any of the aforementioned applicators, wherein the compressible material comprises metal. In certain embodiments, the present invention relates to any of the aforementioned applicators, wherein the compressible material comprises paper. In certain embodiments, the present invention relates to any of the aforementioned applicators, wherein the compressible material is a laminate. In certain embodiments, the present invention relates to any of the aforementioned applicators, wherein the compressible material is a glaminate.

In certain embodiments, the present invention relates to any of the aforementioned applicators, wherein the applicator body further comprises a springing mechanism in the interior of the applicator body, wherein the springing mechanism effects a spring back of the applicator body, thus facilitating the sucking back of components (e.g., the liquid portion and the solid portion) into the applicator body.

In certain embodiments, the present invention relates to any of the aforementioned applicators, wherein the length of the applicator body is between about 1" and about 5". In certain embodiments, the present invention relates to any of the aforementioned applicators, wherein the length of the applicator body is between about 2" and about 4". In certain embodiments, the present invention relates to any of the aforementioned applicators, wherein the length of the applicator body is about 3". In certain embodiments, the present invention relates to any of the aforementioned applicators, wherein the length of the applicator body is about 2". In certain embodiments, the present invention relates to any of the aforementioned applicators, wherein the length of the applicator body is about 1".

In certain embodiments, the present invention relates to any of the aforementioned applicators, wherein the average outer diameter of the applicator body is between about 0.15" and about 0.55". In certain embodiments, the present invention relates to any of the aforementioned applicators, wherein the average outer diameter of the applicator body is about 0.35".

In certain embodiments, the present invention relates to any of the aforementioned applicators, wherein the average wall thickness of the applicator body is between about 0.001" and about 0.1". In certain embodiments, the present invention relates to any of the aforementioned applicators, wherein the average wall thickness of the applicator body is between about 0.01" and about 0.03". In certain embodiments, the present invention relates to any of the aforementioned applicators, wherein the average wall thickness of the applicator body is about 0.02".

In certain embodiments, the present invention relates to any of the aforementioned applicators, wherein the tip is a nozzle tip.

In certain embodiments, the present invention relates to any of the aforementioned applicators, wherein the tip further comprises a brush, a sponge, a foam swab, a porous plastic component, a duck bill tip, a textile mitt or a spray tip affixed to the distal end of the tip.

In certain embodiments, the present invention relates to any of the aforementioned applicators, wherein the tip is a flow-thru brush.

In certain embodiments, the present invention relates to any of the aforementioned applicators, wherein only the tip comprises a storage receptacle for a solid portion. In certain embodiments, the present invention relates to any of the aforementioned applicators, wherein the storage receptacle for a solid portion is at the proximal end of the tip.

In certain embodiments, the present invention relates to any of the aforementioned applicators, wherein the tip further comprises a solid in the storage receptacle for a solid portion. In certain embodiments, the present invention relates to any of the aforementioned applicators, wherein the solid comprises an activated PEG. In certain embodiments, the present invention relates to any of the aforementioned applicators, wherein the solid comprises PEG-SPA or PEG-SG.

In certain embodiments, the present invention relates to any of the aforementioned applicators, wherein the solid comprises PEG-SG. In certain embodiments, the present invention relates to any of the aforementioned applicators, wherein the length of the tip is between about 0.1" and about 2.0". In certain embodiments, the present invention relates to any of the aforementioned applicators, wherein the length of the tip is between about 0.6" and about 1.2". In certain embodiments, the present invention relates to any of the aforementioned applicators, wherein the length of the tip is about 1.0". In certain embodiments, the present invention relates to any of the aforementioned applicators, wherein the length of the tip is about 0.8".

In certain embodiments, the present invention relates to any of the aforementioned applicators, wherein the diameter of the proximal end of the tip is between about 0.15" and about 0.55". In certain embodiments, the present invention relates to any of the aforementioned applicators, wherein the diameter of the proximal end of the tip is about 0.35". In certain embodiments, the present invention relates to any of the aforementioned applicators, wherein the diameter of the proximal end of the tip is about 0.25".

In certain embodiments, the present invention relates to any of the aforementioned applicators, wherein the cap is configured to receive a mixture of the liquid portion and the solid portion.

In certain embodiments, the present invention relates to any of the aforementioned applicators, wherein only the cap comprises a storage receptacle for a solid portion. In certain embodiments, the present invention relates to any of the aforementioned applicators, wherein the storage receptacle for a solid portion is at the proximal end of the cap.

In certain embodiments, the present invention relates to any of the aforementioned applicators, wherein the cap further comprises a solid in the storage receptacle for a solid portion. In certain embodiments, the present invention relates to any of the aforementioned applicators, wherein the solid comprises an activated PEG. In certain embodiments, the present invention relates to any of the aforementioned applicators, wherein the solid comprises PEG-SPA or PEG-SG. In certain embodiments, the present invention relates to any of the aforementioned applicators, wherein the solid comprises PEG-SG.

In certain embodiments, the present invention relates to any of the aforementioned applicators, wherein the cap is configured to receive the liquid portion.

In certain embodiments, the present invention relates to any of the aforementioned applicators, further comprising a solid; wherein the solid is adsorbed onto the interior walls of the storage receptacle for a solid portion. In certain embodiments, the present invention relates to any of the aforementioned applicators, wherein the solid adsorbed onto the interior walls of the storage receptacle for a solid portion comprises an activated PEG. In certain embodiments, the present invention relates to any of the aforementioned applicators, wherein the solid adsorbed onto the interior walls of the storage receptacle for a solid portion comprises PEG-SPA or PEG-SG. In certain embodiments, the present invention relates to any of the aforementioned applicators, wherein the solid adsorbed onto the interior walls of the storage receptacle for a solid portion comprises PEG-SPA.

In certain embodiments, the present invention relates to any of the aforementioned applicators, wherein the storage receptacle for a solid portion comprises a piece of porous plastic upon which a solid has been adsorbed. In certain embodiments, the present invention relates to any of the aforementioned applicators, wherein the solid adsorbed onto the piece of porous plastic comprises an activated PEG. In certain embodiments, the present invention relates to any of the aforementioned applicators, wherein the solid adsorbed onto the piece of porous plastic comprises PEG-SPA or PEG-SG. In certain embodiments, the present invention relates to any of the aforementioned applicators, wherein the solid adsorbed onto the piece of porous plastic comprises PEG-SPA.

In certain embodiments, the present invention relates to any of the aforementioned applicators, wherein the piece of porous plastic is a piece of polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a co-polymer thereof. In certain embodiments, the present invention relates to any of the aforementioned applicators, wherein the piece of porous plastic is a piece of polyester batting or other fibrous filter media material.

In certain embodiments, the present invention relates to any of the aforementioned applicators, wherein the piece of porous plastic has an average diameter between about 0.02" and about 0.32". In certain embodiments, the present invention relates to any of the aforementioned applicators, wherein the piece of porous plastic has an average diameter between about 0.12" and about 0.22". In certain embodiments, the present invention relates to any of the aforementioned applicators, wherein the piece of porous plastic has an average diameter of about 0.17".

In certain embodiments, the present invention relates to any of the aforementioned applicators, wherein the piece of porous plastic has an average length of between about 0.2" and about 0.6". In certain embodiments, the present invention relates to any of the aforementioned applicators, wherein the piece of porous plastic has an average length of between about 0.3" and about 0.5". In certain embodiments, the present invention relates to any of the aforementioned applicators, wherein the piece of porous plastic has an average length of about 0.4".

In certain embodiments, the present invention relates to any of the aforementioned applicators, wherein the applicator body comprises a friable seal.

In certain embodiments, the present invention relates to any of the aforementioned applicators, wherein the friable seal comprises plastic. In certain embodiments, the present invention relates to any of the aforementioned applicators, wherein the friable seal comprises metal. In certain embodiments, the present invention relates to any of the aforementioned applicators, wherein the exterior surface of the friable seal is coated with a wax or a plastic.

In certain embodiments, the present invention relates to any of the aforementioned applicators, wherein the friable seal is at the distal end of the applicator body. In certain embodiments, the present invention relates to any of the aforementioned applicators, wherein the friable seal is less than 0.1" from the distal end of the applicator body. In certain embodiments, the present invention relates to any of the aforementioned applicators, wherein the friable seal is less than 0.25" from the distal end of the applicator body. In certain embodiments, the present invention relates to any of the aforementioned applicators, wherein the friable seal is less than 0.50" from the distal end of the applicator body. In certain embodiments, the present invention relates to any of the aforementioned applicators, wherein the friable seal is about 0.75" from the distal end of the applicator body.

In certain embodiments, the present invention relates to any of the aforementioned applicators, wherein the tip is designed so as to break the friable seal when the distal end of the applicator body is connected to the proximal end of the tip.

In certain embodiments, the present invention relates to any of the aforementioned applicators, wherein the applicator body comprises a removable separator.

Another aspect of the present invention relates to an applicator comprising an applicator body and a tip; wherein the applicator body comprises a first storage receptacle for a mixture of a first liquid portion and a second liquid portion, a closed proximal end, and an open distal end; and the tip comprises an open distal end, and an open proximal end connected to the open distal end of the applicator body.

Another aspect of the present invention relates to an applicator comprising an applicator body and a tip; wherein the applicator body comprises a first storage receptacle for a first liquid portion, a second storage receptacle for a second liquid portion, a closed proximal end, and an open distal end; and the tip comprises an open distal end, and an open proximal end connected to the open distal end of the applicator body.

In certain embodiments, the present invention relates to any of the aforementioned applicators, further comprising additional storage receptacles.

In certain embodiments, the present invention relates to any of the aforementioned applicators, further comprising a screen or filter placed in the tip.

In certain embodiments, the present invention relates to any of the aforementioned applicators, further comprising a screen or filter placed between the open distal end of the applicator body and the open proximal end of the tip.

In certain embodiments, the present invention relates to any of the aforementioned applicators, wherein the first storage receptacle is a crushable ampoule.

In certain embodiments, the present invention relates to any of the aforementioned applicators, wherein the second storage receptacle is a crushable ampoule.

In certain embodiments, the present invention relates to any of the aforementioned applicators, wherein the applicator body further comprises a solid.

In certain embodiments, the present invention relates to any of the aforementioned applicators, wherein the applicator body is divided by friable seals into a proximal compartment, a middle compartment, and a distal compartment; the proximal compartment and the middle compartment are separated by a first friable seal; the middle compartment and the distal compartment are separated by a second friable seal; the proximal compartment is the first storage receptacle; and the middle compartment is the second storage receptacle.

In certain embodiments, the present invention relates to any of the aforementioned applicators, wherein the applicator body further comprises a mixture of a first liquid portion and a second liquid portion in the first storage receptacle. In certain embodiments, the present invention relates to any of the aforementioned applicators, wherein the applicator body further comprises a first liquid portion in the first storage receptacle. In certain embodiments, the present invention relates to any of the aforementioned applicators, wherein the applicator body further comprises a second liquid portion in the second storage receptacle.

In certain embodiments, the present invention relates to any of the aforementioned applicators, wherein the first liquid portion comprises a polyalkyleneimine, epoxy-resin component or polyurethane prepolymer. In certain embodiments, the present invention relates to any of the aforementioned applicators, wherein the first liquid portion comprises a polyalkyleneimine. In certain embodiments, the present invention relates to any of the aforementioned applicators, wherein the first liquid portion comprises PEI. In certain embodiments, the present invention relates to any of the aforementioned applicators, wherein the second liquid portion comprises a buffer or a curing agent. In certain embodiments, the present invention relates to any of the aforementioned applicators, wherein the second liquid portion comprises a buffer.

In certain embodiments, the present invention relates to any of the aforementioned applicators, wherein the distal compartment comprises a solid.

In certain embodiments, the present invention relates to any of the aforementioned applicators, wherein the distal compartment comprises a solid in a crushable ampoule. In certain embodiments, the present invention relates to any of the aforementioned applicators, wherein the crushable ampoule is glass.

In certain embodiments, the present invention relates to any of the aforementioned applicators, wherein the solid comprises an activated PEG. In certain embodiments, the present invention relates to any of the aforementioned applicators, wherein the solid comprises PEG-SPA or PEG-SG. In certain embodiments, the present invention relates to any of the aforementioned applicators, wherein the solid comprises PEG-SG.

In certain embodiments, the present invention relates to any of the aforementioned applicators, wherein the applicator body is tubular.

In certain embodiments, the present invention relates to any of the aforementioned applicators, wherein the applicator body is made from a compressible material, wherein the compressible material permits manual pressurization. In certain embodiments, the present invention relates to any of the aforementioned applicators, wherein the compressible material comprises plastic. In certain embodiments, the present invention relates to any of the aforementioned applicators, wherein the compressible material comprises metal. In certain embodiments, the present invention relates to any of the aforementioned applicators, wherein the compressible material is a laminate. In certain embodiments, the present invention relates to any of the aforementioned applicators, wherein the compressible material is a glaminate.

In certain embodiments, the present invention relates to any of the aforementioned applicators, wherein the length of the applicator body is between about 1" and about 9". In certain embodiments, the present invention relates to any of the aforementioned applicators, wherein the length of the applicator body is about 9". In certain embodiments, the present invention relates to any of the aforementioned applicators, wherein the length of the applicator body is about 8". In certain embodiments, the present invention relates to any of the aforementioned applicators, wherein the length of the applicator body is about 7". In certain embodiments, the present invention relates to any of the aforementioned applicators, wherein the length of the applicator body is about 6". In certain embodiments, the present invention relates to any of the aforementioned applicators, wherein the length of the applicator body is about 5". In certain embodiments, the present invention relates to any of the aforementioned applicators, wherein the length of the applicator body is about 4". In certain embodiments, the present invention relates to any of the aforementioned applicators, wherein the length of the applicator body is about 3". In certain embodiments, the present invention relates to any of the aforementioned applicators, wherein the length of the applicator body is about 2". In certain embodiments, the present invention relates to any of the aforementioned applicators, wherein the length of the applicator body is about 1".

In certain embodiments, the present invention relates to any of the aforementioned applicators, wherein the average outer diameter of the applicator body is between about 0.1" and about 2". In certain embodiments, the present invention relates to any of the aforementioned applicators, wherein the average outer diameter of the applicator body is about 1.75". In certain embodiments, the present invention relates to any of the aforementioned applicators, wherein the average outer diameter of the applicator body is about 1.50". In certain embodiments, the present invention relates to any of the aforementioned applicators, wherein the average outer diameter of the applicator body is about 1.25". In certain embodiments, the present invention relates to any of the aforementioned applicators, wherein the average outer diameter of the applicator body is about 1". In certain embodiments, the present invention relates to any of the aforementioned applicators, wherein the average outer diameter of the applicator body is about 0.75". In certain embodiments, the present invention relates to any of the aforementioned applicators, wherein the average outer diameter of the applicator body is about 0.5". In certain embodiments, the present invention relates to any of the aforementioned applicators, wherein the average outer diameter of the applicator body is about 0.25".

In certain embodiments, the present invention relates to any of the aforementioned applicators, wherein the average wall thickness of the applicator body is between about 0.001" and about 0.1". In certain embodiments, the present invention relates to any of the aforementioned applicators, wherein the average wall thickness of the applicator body is between about 0.01" and about 0.03". In certain embodiments, the present invention relates to any of the aforementioned applicators, wherein the average wall thickness of the applicator body is about 0.02".

In certain embodiments, the present invention relates to any of the aforementioned applicators, wherein the tip is a nozzle tip. In certain embodiments, the present invention relates to any of the aforementioned applicators, wherein the tip is a flow-thru brush.

In certain embodiments, the present invention relates to any of the aforementioned applicators, wherein the tip further comprises a cannula, an inoculating loop, a brush, a sponge, a foam swab, a porous plastic component, a duck bill tip, a textile mitt or a spray tip affixed to the distal end of the tip. In certain embodiments, the present invention relates to any of the aforementioned applicators, wherein the tip comprises a cannula. In certain embodiments, the present invention relates to any of the aforementioned applicators, wherein the tip comprises an inoculating loop.

In certain embodiments, the present invention relates to any of the aforementioned applicators, wherein the length of the tip is between about 0.1" and about 9.0". In certain embodiments, the present invention relates to any of the aforementioned applicators, wherein the length of the tip is about 7.5". In certain embodiments, the present invention relates to any of the aforementioned applicators, wherein the length of the tip is about 5.0". In certain embodiments, the present invention relates to any of the aforementioned applicators, wherein the length of the tip is about 2.5". In certain embodiments, the present invention relates to any of the aforementioned applicators, wherein the length of the tip is about 1.0". In certain embodiments, the present invention relates to any of the aforementioned applicators, wherein the length of the tip is about 0.5".

In certain embodiments, the present invention relates to any of the aforementioned applicators, wherein the diameter of the proximal end of the tip is between about 0.15" and about 0.55". In certain embodiments, the present invention relates to any of the aforementioned applicators, wherein the diameter of the proximal end of the tip is about 0.35". In certain embodiments, the present invention relates to any of the aforementioned applicators, wherein the diameter of the proximal end of the tip is about 0.25".

In certain embodiments, the present invention relates to any of the aforementioned applicators, wherein the first friable seal comprises wax. In certain embodiments, the present invention relates to any of the aforementioned applicators, wherein the second friable seal comprises wax. In certain embodiments, the present invention relates to any of the aforementioned applicators, wherein the first friable seal comprises wax; and the second friable seal comprises wax. In certain embodiments, the present invention relates to any of the aforementioned applicators, wherein the wax is beeswax, carnauba (a vegetable wax) or paraffin (a mineral wax).

In certain embodiments, the present invention relates to any of the aforementioned applicators, wherein the first friable seal comprises wax and metal particles. In certain embodiments, the present invention relates to any of the aforementioned applicators, wherein the first friable seal comprises wax and ferrous metal particles. In certain embodiments, the present invention relates to any of the aforementioned applicators, wherein the second friable seal comprises wax and metal particles. In certain embodiments, the present invention relates to any of the aforementioned applicators, wherein the second friable seal comprises wax and ferrous metal particles.

In certain embodiments, the present invention relates to any of the aforementioned applicators, wherein the first friable seal consists essentially of wax. In certain embodiments, the present invention relates to any of the aforementioned applicators, wherein the second friable seal consists essentially of wax. In certain embodiments, the present invention relates to any of the aforementioned applicators, wherein the first friable seal consists essentially of wax; and the second friable seal consists essentially of wax. In certain embodiments, the present invention relates to any of the aforementioned applicators, wherein the wax is beeswax, carnauba (a vegetable wax) or paraffin (a mineral wax).

In certain embodiments, the present invention relates to any of the aforementioned applicators, wherein the first friable seal consists essentially of wax and metal particles. In certain embodiments, the present invention relates to any of the aforementioned applicators, wherein the first friable seal consists essentially of wax and ferrous metal particles. In certain embodiments, the present invention relates to any of the aforementioned applicators, wherein the second friable seal consists essentially of wax and metal particles. In certain embodiments, the present invention relates to any of the aforementioned applicators, wherein the second friable seal consists essentially of wax and ferrous metal particles.

In certain embodiments, the present invention relates to any of the aforementioned applicators, wherein both friable seals comprise plastic. In certain embodiments, the present invention relates to any of the aforementioned applicators, wherein both friable seals comprises metal.

In certain embodiments, the present invention relates to any of the aforementioned applicators, wherein the average thickness of the first friable seal is about 10 mm. In certain embodiments, the present invention relates to any of the aforementioned applicators, wherein the average thickness of the first friable seal is about 7.5 mm. In certain embodiments, the present invention relates to any of the aforementioned applicators, wherein the average thickness of the first friable seal is about 5 mm. In certain embodiments, the present invention relates to any of the aforementioned applicators, wherein the average thickness of the first friable seal is about 2.5 mm. In certain embodiments, the present invention relates to any of the aforementioned applicators, wherein the average thickness of the first friable seal is about 1 mm. In certain embodiments, the present invention relates to any of the aforementioned applicators, wherein the average thickness of the second friable seal is about 10 mm. In certain embodiments, the present invention relates to any of the aforementioned applicators, wherein the average thickness of the second friable seal is about 7.5 mm. In certain embodiments, the present invention relates to any of the aforementioned applicators, wherein the average thickness of the second friable seal is about 5 mm. In certain embodiments, the present invention relates to any of the aforementioned applicators, wherein the average thickness of the second friable seal is about 2.5 mm. In certain embodiments, the present invention relates to any of the aforementioned applicators, wherein the average thickness of the second friable seal is about 1 mm.

In certain embodiments, the present invention relates to any of the aforementioned applicators, wherein the first friable seal is about 1" from the proximal end of the applicator body. In certain embodiments, the present invention relates to any of the aforementioned applicators, wherein the first friable seal is about 2" from the proximal end of the applicator body. In certain embodiments, the present invention relates to any of the aforementioned applicators, wherein the first friable seal is about 3" from the proximal end of the applicator body. In certain embodiments, the present invention relates to any of the aforementioned applicators, wherein the first friable seal is about 4" from the proximal end of the applicator body. In certain embodiments, the present invention relates to any of the aforementioned applicators, wherein the first friable seal is about 5" from the proximal end of the applicator body. In certain embodiments, the present invention relates to any of the aforementioned applicators, wherein the first friable seal is about 6" from the proximal end of the applicator body.

In certain embodiments, the present invention relates to any of the aforementioned applicators, wherein the first friable seal is about 7" from the proximal end of the applicator body. In certain embodiments, the present invention relates to any of the aforementioned applicators, wherein the first friable seal is about 8" from the proximal end of the applicator body. In certain embodiments, the present invention relates to any of the aforementioned applicators, wherein the first friable seal is about 9" from the proximal end of the applicator body.

In certain embodiments, the present invention relates to any of the aforementioned applicators, wherein the second friable seal is about 1" from the distal end of the applicator body. In certain embodiments, the present invention relates to any of the aforementioned applicators, wherein the second friable seal is about 2" from the distal end of the applicator body. In certain embodiments, the present invention relates to any of the aforementioned applicators, wherein the second friable seal is about 3" from the distal end of the applicator body. In certain embodiments, the present invention relates to any of the aforementioned applicators, wherein the second friable seal is about 4" from the distal end of the applicator body. In certain embodiments, the present invention relates to any of the aforementioned applicators, wherein the second friable seal is about 5" from the distal end of the applicator body. In certain embodiments, the present invention relates to any of the aforementioned applicators, wherein the second friable seal is about 6" from the distal end of the applicator body. In certain embodiments, the present invention relates to any of the aforementioned applicators, wherein the second friable seal is about 7" from the distal end of the applicator body. In certain embodiments, the present invention relates to any of the aforementioned applicators, wherein the second friable seal is about 8" from the distal end of the applicator body. In certain embodiments, the present invention relates to any of the aforementioned applicators, wherein the second friable seal is about 9" from the distal end of the applicator body.

Another aspect of the present invention relates to a handheld brush applicator comprising a handle, a brush and a solid;
wherein the brush is connected to one end of the handle; and the solid is adsorbed onto the brush.

In certain embodiments, the present invention relates to any of the aforementioned applicators, wherein the solid comprises an activated PEG. In certain embodiments, the present invention relates to any of the aforementioned applicators, wherein the solid comprises PEG-SPA or PEG-SG. In certain embodiments, the present invention relates to any of the aforementioned applicators, wherein the solid comprises PEG-SG.

One aspect of the present invention relates to an applicator comprising an applicator body, a tip and a bladder;
wherein the applicator body comprises a storage receptacle for a liquid portion, a closed proximal end, an open distal end, and a friable seal or a removable separator separating the storage receptacle for the liquid portion from the open distal end; the tip comprises an open proximal end connected to the open distal end of the bladder, and an open distal end; the bladder comprises an open distal end that connects to the tip, and an open proximal end that connects to the applicator body.

In certain embodiments, the present invention relates to any of the aforementioned applicators, wherein the applicator body is tubular. In certain embodiments, the present invention relates to any of the aforementioned applicators, wherein the applicator body is a plastic ampoule.

In certain embodiments, the present invention relates to any of the aforementioned applicators, wherein the applicator body further comprises a liquid in the storage receptacle for a liquid portion. In certain embodiments, the present invention relates to any of the aforementioned applicators, wherein the liquid comprises a polyalkyleneimine. In certain embodiments, the present invention relates to any of the aforementioned applicators, wherein the liquid comprises PEI.

In certain embodiments, the present invention relates to any of the aforementioned applicators, wherein the applicator body is made from a compressible material, wherein the compressible material permits manual pressurization. In certain embodiments, the present invention relates to any of the aforementioned applicators, wherein the compressible material comprises plastic. In certain embodiments, the present invention relates to any of the aforementioned applicators, wherein the compressible material comprises metal. In certain embodiments, the present invention relates to any of the aforementioned applicators, wherein the compressible material comprises paper. In certain embodiments, the present invention relates to any of the aforementioned applicators, wherein the compressible material is a laminate. In certain embodiments, the present invention relates to any of the aforementioned applicators, wherein the compressible material is a glaminate.

In certain embodiments, the present invention relates to any of the aforementioned applicators, wherein the applicator body further comprises a springing mechanism in the interior of the applicator body, wherein the springing mechanism effects a spring back of the applicator body, thus facilitating the sucking back of components (e.g., the liquid portion and the solid portion) into the applicator body.

In certain embodiments, the present invention relates to any of the aforementioned applicators, wherein the length of the applicator body is between about 1" and about 5". In certain embodiments, the present invention relates to any of the aforementioned applicators, wherein the length of the applicator body is between about 2" and about 4". In certain embodiments, the present invention relates to any of the aforementioned applicators, wherein the length of the applicator body is about 3". In certain embodiments, the present invention relates to any of the aforementioned applicators, wherein the length of the applicator body is about 2". In certain embodiments, the present invention relates to any of the aforementioned applicators, wherein the length of the applicator body is about 1".

In certain embodiments, the present invention relates to any of the aforementioned applicators, wherein the average outer diameter of the applicator body is between about 0.15" and about 0.55". In certain embodiments, the present invention relates to any of the aforementioned applicators, wherein the average outer diameter of the applicator body is about 0.35".

In certain embodiments, the present invention relates to any of the aforementioned applicators, wherein the average wall thickness of the applicator body is between about 0.001" and about 0.1". In certain embodiments, the present invention relates to any of the aforementioned applicators, wherein the average wall thickness of the applicator body is between about 0.01" and about 0.03". In certain embodiments, the present invention relates to any of the aforementioned applicators, wherein the average wall thickness of the applicator body is about 0.02".

In certain embodiments, the present invention relates to any of the aforementioned applicators, wherein the tip is a nozzle tip.

In certain embodiments, the present invention relates to any of the aforementioned applicators, wherein the tip further comprises a brush, a sponge, a foam swab, a porous plastic component, a duck bill tip, a textile mitt or a spray tip affixed to the distal end of the tip.

In certain embodiments, the present invention relates to any of the aforementioned applicators, wherein the tip is a flow-thru brush.

In certain embodiments, the present invention relates to any of the aforementioned applicators, wherein the bladder comprises a storage receptacle for a solid portion. In certain embodiments, the present invention relates to any of the aforementioned applicators, wherein the bladder further comprises a solid in the storage receptacle for a solid portion. In certain embodiments, the present invention relates to any of the aforementioned applicators, wherein the solid comprises an activated PEG. In certain embodiments, the present invention relates to any of the aforementioned applicators, wherein the solid comprises PEG-SPA or PEG-SG. In certain embodiments, the present invention relates to any of the aforementioned applicators, wherein the solid comprises PEG-SG.

In certain embodiments, the present invention relates to any of the aforementioned applicators, wherein the length of the tip is between about 0.1" and about 2.0". In certain embodiments, the present invention relates to any of the aforementioned applicators, wherein the length of the tip is between about 0.6" and about 1.2". In certain embodiments, the present invention relates to any of the aforementioned applicators, wherein the length of the tip is about 1.0". In certain embodiments, the present invention relates to any of the aforementioned applicators, wherein the length of the tip is about 0.8".

In certain embodiments, the present invention relates to any of the aforementioned applicators, wherein the diameter of the proximal end of the tip is between about 0.15" and about 0.55". In certain embodiments, the present invention relates to any of the aforementioned applicators, wherein the diameter of the proximal end of the tip is about 0.35". In certain embodiments, the present invention relates to any of the aforementioned applicators, wherein the diameter of the proximal end of the tip is about 0.25".

In certain embodiments, the present invention relates to any of the aforementioned applicators, further comprising a solid; wherein the solid is adsorbed onto the interior walls of the bladder. In certain embodiments, the present invention relates to any of the aforementioned applicators, wherein the solid adsorbed onto the interior walls of the bladder comprises an activated PEG. In certain embodiments, the present invention relates to any of the aforementioned applicators, wherein the solid adsorbed onto the interior walls of the bladder comprises PEG-SPA or PEG-SG. In certain embodiments, the present invention relates to any of the aforementioned applicators, wherein the solid adsorbed onto the interior walls of the bladder comprises PEG-SPA.

In certain embodiments, the present invention relates to the aforementioned applicator, wherein the storage receptacle for a solid portion comprises the interior aspect of the bladder.

In certain embodiments, the present invention relates to any of the aforementioned applicators, wherein the storage receptacle for a solid portion comprises a piece of porous plastic upon which a solid has been adsorbed. In certain embodiments, the present invention relates to any of the aforementioned applicators, wherein the solid adsorbed onto the piece of porous plastic comprises an activated PEG. In certain embodiments, the present invention relates to any of the aforementioned applicators, wherein the solid adsorbed onto the piece of porous plastic comprises PEG-SPA or PEG-SG. In certain embodiments, the present invention relates to any of the aforementioned applicators, wherein the solid adsorbed onto the piece of porous plastic comprises PEG-SPA.

In certain embodiments, the present invention relates to any of the aforementioned applicators, wherein the piece of porous plastic is a piece of polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a co-polymer thereof. In certain embodiments, the present invention relates to any of the aforementioned applicators, wherein the piece of porous plastic is a piece of polyester batting or other fibrous filter media material.

In certain embodiments, the present invention relates to any of the aforementioned applicators, wherein the piece of porous plastic has an average diameter between about 0.02" and about 0.32". In certain embodiments, the present invention relates to any of the aforementioned applicators, wherein the piece of porous plastic has an average diameter between about 0.12" and about 0.22". In certain embodiments, the present invention relates to any of the aforementioned applicators, wherein the piece of porous plastic has an average diameter of about 0.17".

In certain embodiments, the present invention relates to any of the aforementioned applicators, wherein the piece of porous plastic has an average length of between about 0.2" and about 0.6". In certain embodiments, the present invention relates to any of the aforementioned applicators, wherein the piece of porous plastic has an average length of between about 0.3" and about 0.5". In certain embodiments, the present invention relates to any of the aforementioned applicators, wherein the piece of porous plastic has an average length of about 0.4".

In certain embodiments, the present invention relates to any of the aforementioned applicators, wherein the applicator body comprises a friable seal.

In certain embodiments, the present invention relates to any of the aforementioned applicators, wherein the friable seal comprises plastic. In certain embodiments, the present invention relates to any of the aforementioned applicators, wherein the friable seal comprises metal. In certain embodiments, the present invention relates to any of the aforementioned applicators, wherein the exterior surface of the friable seal is coated with a wax or a plastic.

In certain embodiments, the present invention relates to any of the aforementioned applicators, wherein the friable seal is at the distal end of the applicator body. In certain embodiments, the present invention relates to any of the aforementioned applicators, wherein the friable seal is less than 0.1" from the distal end of the applicator body. In certain embodiments, the present invention relates to any of the aforementioned applicators, wherein the friable seal is less than 0.25" from the distal end of the applicator body. In certain embodiments, the present invention relates to any of the aforementioned applicators, wherein the friable seal is less than 0.50" from the distal end of the applicator body. In certain embodiments, the present invention relates to any of the aforementioned applicators, wherein the friable seal is about 0.75" from the distal end of the applicator body.

In certain embodiments, the present invention relates to any of the aforementioned applicators, wherein the friable seal comprises wax. In certain embodiments, the present invention relates to any of the aforementioned applicators, wherein the wax is beeswax, carnauba (a vegetable wax) or paraffin (a mineral wax).

In certain embodiments, the present invention relates to any of the aforementioned applicators, wherein the friable seal comprises wax and metal particles. In certain embodiments, the present invention relates to any of the aforementioned applicators, wherein the friable seal comprises wax and ferrous metal particles.

In certain embodiments, the present invention relates to any of the aforementioned applicators, wherein the friable seal consists essentially of wax. In certain embodiments, the present invention relates to any of the aforementioned applicators, wherein the wax is beeswax, carnauba (a vegetable wax) or paraffin (a mineral wax).

In certain embodiments, the present invention relates to any of the aforementioned applicators, wherein the average thickness of the friable seal is about 10 mm. In certain embodiments, the present invention relates to any of the aforementioned applicators, wherein the average thickness of the friable seal is about 7.5 mm. In certain embodiments, the present invention relates to any of the aforementioned applicators, wherein the average thickness of the friable seal is about 5 mm. In certain embodiments, the present invention relates to any of the aforementioned applicators, wherein the average thickness of the friable seal is about 2.5 mm. In certain embodiments, the present invention relates to any of the aforementioned applicators, wherein the average thickness of the friable seal is about 1 mm.

In certain embodiments, the present invention relates to any of the aforementioned applicators, wherein the applicator body comprises a removable separator.

In certain embodiments, the present invention relates to any of the aforementioned applicators, further comprising a cap which engages the proximal end of the tip; and further comprises a solid receptacle.

As is apparent from the description of the plural embodiments above, remarkable multi-component applicator assemblies are herein provided. While such multi-component applicators can be used for dispensing hydrogels, as discussed in detail below, the present invention is also applicable to the dispensing any plural component mixtures which are to be mixed prior to use and which may need to be stored separately. In particular, the present invention includes an applicator assembly for concurrently dispensing plural flowable component materials, which overcomes shortcomings associated with known multiple component dispensers. For example, the present invention is applicable to dispensing two-component adhesives, sealants, coatings, and potting compounds, such as epoxies, urethanes, acrylics, polysulfides, polyesters, and silicones, as well as other adhesive or sealant materials and the like.

Epoxy adhesives are an example of a multiple-component adhesive, and more generally of a multiple-component product, that requires the component materials to be stored individually prior to use, and which must be mixed in accordance with a specific ratio prior to use. Epoxy adhesives typically include an epoxy-resin component and a curing-agent component, such that when mixed together in proper proportions, the epoxy curative hardens in place. With this in mind, the applicators described herein may be used as epoxy-adhesive dispensing-devices, having separate storage locations for the epoxy-resin component and the curing-agent component, and a means for dispensing together the separate components and in accordance with the proper ratio for curing.

In addition, a variety of polyurethanes, such as those which are useful for bonding to porous and non-porous substrates, also requires the component materials to be stored individually and mixed in accordance with a specific ratio for usage. Polyurethane adhesive compositions typically comprise at least one polyurethane prepolymer and a curing agent.

Further, fibrin sealants, which are formed from blood plasma components, comprise a first component containing fibrinogen and Factor XIII, and a second component, which usually includes thrombin and calcium ions, may also be delivered via the applicators disclosed herein. It is well known that fibrinogen is capable of polymerizing and being cross-linked to form a fibrin clot when the proper components are mixed. The necessary additional factors to simulate relevant portions of the natural blood coagulation cascade can be suitably distributed between the fibrinogen and thrombin components. See, for example, Antanavich et al. U.S. Pat. No. 5,585,007, which is hereby incorporated by reference, provides an extensive discussion of fibrinogen sealant preparation (column 1, line 20 to column 4, line 62) and applicators (column 4 line 62 to column 5, line 14).

Selected Compositions of Matter

One aspect of the invention relates to a composition comprising a solid and an activated PEG, wherein the activated PEG is adsorbed onto the solid.

In certain embodiments, the present invention relates to the aforementioned solid, wherein the solid is a piece of porous plastic. In certain embodiments, the present invention relates to the aforementioned solid, wherein the porous plastic is a polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a co-polymer thereof. In certain embodiments, the present invention relates to the aforementioned solid, wherein the piece of porous plastic is a piece of polyester batting or other fibrous filter media material.

Selected Methods

One aspect of the invention relates to a method of using an applicator to apply a hydrogel to a surface;

wherein the applicator comprises an applicator body, a tip and a cap; the applicator body comprises a storage receptacle for a liquid portion, a closed proximal end, an open distal end, and a friable seal separating the storage receptacle for the liquid portion from the open distal end; the tip comprises an open proximal end connected to the open distal end of the applicator body, and an open distal end; the cap covers the open distal end of the tip in a non-airtight manner; and the tip or the cap comprises a storage receptacle for a solid portion;

comprising the steps of:

squeezing the applicator body, thereby breaking the friable seal, and causing the solid to come into contact with the liquid portion, thereby forming a liquid pre-hydrogel mixture;

applying the liquid pre-hydrogel mixture to a surface, wherein the pre-hydrogel mixture gels to form a hydrogel on the surface.

In certain embodiments, the present invention relates to any of the aforementioned methods, further comprising the step of releasing the applicator body.

Another aspect of the invention relates to a method of using an applicator to apply a hydrogel to a surface;

wherein the applicator comprises an applicator body, a tip and a cap; the applicator body comprises a storage receptacle for a liquid portion, a closed proximal end, an open distal end, and a removable separator separating the storage receptacle for the liquid portion from the open distal end; the tip comprises an open proximal end connected to the open distal end of the applicator body, and an open distal end; the cap covers the open distal end of the tip in a non-airtight manner; and the tip or the cap comprises a storage receptacle for a solid portion;

comprising the steps of:

removing the removable separator, causing the solid to come into contact with the liquid portion, thereby forming a liquid pre-hydrogel mixture;

applying the liquid pre-hydrogel mixture to a surface, wherein the pre-hydrogel mixture gels to form a hydrogel on the surface.

In certain embodiments, the present invention relates to any of the aforementioned methods, wherein the applicator body is tubular. In certain embodiments, the present invention relates to any of the aforementioned methods, wherein the applicator body is a plastic ampoule.

In certain embodiments, the present invention relates to any of the aforementioned methods, wherein the applicator body further comprises a liquid in the storage receptacle for a liquid portion. In certain embodiments, the present invention relates to any of the aforementioned methods, wherein the liquid comprises a polyalkyleneimine. In certain embodiments, the present invention relates to any of the aforementioned methods, wherein the liquid comprises PEI.

In certain embodiments, the present invention relates to any of the aforementioned methods, wherein the applicator body is made from a compressible material, wherein the compressible material permits manual pressurization. In certain embodiments, the present invention relates to any of the aforementioned methods, wherein the compressible material comprises plastic. In certain embodiments, the present invention relates to any of the aforementioned methods, wherein the compressible material comprises metal. In certain embodiments, the present invention relates to any of the aforementioned methods, wherein the compressible material comprises paper. In certain embodiments, the present invention relates to any of the aforementioned methods, wherein the compressible material is a laminate. In certain embodiments, the present invention relates to any of the aforementioned methods, wherein the compressible material is a glaminate.

In certain embodiments, the present invention relates to any of the aforementioned methods, wherein the applicator body further comprises a springing mechanism in the interior of the applicator body, wherein the springing mechanism effects a spring back of the applicator body, thus facilitating the sucking back of components (e.g., the liquid portion and the solid portion) into the applicator body.

In certain embodiments, the present invention relates to any of the aforementioned methods, wherein the length of the applicator body is between about 1" and about 5". In certain embodiments, the present invention relates to any of the aforementioned methods, wherein the length of the applicator body is between about 2" and about 4". In certain embodiments, the present invention relates to any of the aforementioned methods, wherein the length of the applicator body is about 3". In certain embodiments, the present invention relates to any of the aforementioned methods, wherein the length of the applicator body is about 2". In certain embodiments, the present invention relates to any of the aforementioned methods, wherein the length of the applicator body is about 1".

In certain embodiments, the present invention relates to any of the aforementioned methods, wherein the average outer diameter of the applicator body is between about 0.15" and about 0.55". In certain embodiments, the present invention relates to any of the aforementioned methods, wherein the average outer diameter of the applicator body is about 0.35".

In certain embodiments, the present invention relates to any of the aforementioned methods, wherein the average wall thickness of the applicator body is between about 0.001" and about 0.1". In certain embodiments, the present invention relates to any of the aforementioned methods, wherein the average wall thickness of the applicator body is between about 0.01" and about 0.03". In certain embodiments, the present invention relates to any of the aforementioned methods, wherein the average wall thickness of the applicator body is about 0.02".

In certain embodiments, the present invention relates to any of the aforementioned methods, wherein the tip is a nozzle tip.

In certain embodiments, the present invention relates to any of the aforementioned methods, wherein the tip further comprises a brush, a sponge, a foam swab, a porous plastic component, a duck bill tip, a textile mitt or a spray tip affixed to the distal end of the tip.

In certain embodiments, the present invention relates to any of the aforementioned methods, wherein the tip is a flow-thru brush.

In certain embodiments, the present invention relates to any of the aforementioned methods, wherein only the tip comprises a storage receptacle for a solid portion. In certain embodiments, the present invention relates to any of the aforementioned methods, wherein the storage receptacle for a solid portion is at the proximal end of the tip.

In certain embodiments, the present invention relates to any of the aforementioned methods, wherein the tip further comprises a solid in the storage receptacle for a solid portion. In certain embodiments, the present invention relates to any of the aforementioned methods, wherein the solid comprises an activated PEG. In certain embodiments, the present invention relates to any of the aforementioned methods, wherein the solid comprises PEG-SPA or PEG-SG. In certain embodiments, the present invention relates to any of the aforementioned methods, wherein the solid comprises PEG-SG.

In certain embodiments, the present invention relates to any of the aforementioned methods, wherein the length of the tip is between about 0.1" and about 2.0". In certain embodiments, the present invention relates to any of the aforementioned methods, wherein the length of the tip is between about 0.6" and about 1.2". In certain embodiments, the present invention relates to any of the aforementioned methods, wherein the length of the tip is about 1.0". In certain embodiments, the present invention relates to any of the aforementioned methods, wherein the length of the tip is about 0.8".

In certain embodiments, the present invention relates to any of the aforementioned methods, wherein the diameter of the proximal end of the tip is between about 0.15" and about 0.55". In certain embodiments, the present invention relates to any of the aforementioned methods, wherein the diameter of the proximal end of the tip is about 0.35". In certain embodiments, the present invention relates to any of the aforementioned methods, wherein the diameter of the proximal end of the tip is about 0.25".

In certain embodiments, the present invention relates to any of the aforementioned methods, wherein the cap is configured to receive a mixture of the liquid portion and the solid portion.

In certain embodiments, the present invention relates to any of the aforementioned methods, wherein only the cap comprises a storage receptacle for a solid portion. In certain embodiments, the present invention relates to any of the aforementioned methods, wherein the storage receptacle for a solid portion is at the proximal end of the cap.

In certain embodiments, the present invention relates to any of the aforementioned methods, wherein the cap further comprises a solid in the storage receptacle for a solid portion. In certain embodiments, the present invention relates to any of the aforementioned methods, wherein the solid comprises an activated PEG. In certain embodiments, the present invention relates to any of the aforementioned methods, wherein the solid comprises PEG-SPA or PEG-SG. In certain embodiments, the present invention relates to any of the aforementioned methods, wherein the solid comprises PEG-SG.

In certain embodiments, the present invention relates to any of the aforementioned methods, wherein the cap is configured to receive the liquid portion.

In certain embodiments, the present invention relates to any of the aforementioned methods, wherein the solid is adsorbed onto the interior walls of the storage receptacle for a solid portion. In certain embodiments, the present invention relates to any of the aforementioned methods, wherein the solid adsorbed onto the interior walls of the storage receptacle for a solid portion comprises an activated PEG. In certain embodiments, the present invention relates to any of the aforementioned methods, wherein the solid adsorbed onto the interior walls of the storage receptacle for a solid portion comprises PEG-SPA or PEG-SG. In certain embodiments, the present invention relates to any of the aforementioned methods, wherein the solid adsorbed onto the interior walls of the storage receptacle for a solid portion comprises PEG-SPA.

In certain embodiments, the present invention relates to any of the aforementioned methods, wherein the storage receptacle for a solid portion comprises a piece of porous plastic upon which a solid has been adsorbed. In certain embodiments, the present invention relates to any of the aforementioned methods, wherein the solid adsorbed onto the piece of porous plastic comprises an activated PEG. In certain embodiments, the present invention relates to any of the aforementioned methods, wherein the solid adsorbed onto the piece of porous plastic comprises PEG-SPA or PEG-SG. In certain embodiments, the present invention relates to any of the aforementioned methods, wherein the solid adsorbed onto the piece of porous plastic comprises PEG-SPA.

In certain embodiments, the present invention relates to any of the aforementioned applicators, wherein the piece of porous plastic is a piece of polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a co-polymer thereof. In certain embodiments, the present invention relates to any of the aforementioned methods, wherein the piece of porous plastic is a piece of polyester batting or other fibrous filter media material.

In certain embodiments, the present invention relates to any of the aforementioned methods, wherein the piece of porous plastic has an average diameter between about 0.02" and about 0.32". In certain embodiments, the present invention relates to any of the aforementioned methods, wherein the piece of porous plastic has an average diameter between about 0.12" and about 0.22". In certain embodiments, the present invention relates to any of the aforementioned methods, wherein the piece of porous plastic has an average diameter of about 0.17".

In certain embodiments, the present invention relates to any of the aforementioned methods, wherein the piece of porous plastic has an average length of between about 0.2" and about 0.6". In certain embodiments, the present invention relates to any of the aforementioned methods, wherein the piece of porous plastic has an average length of between about 0.3" and about 0.5". In certain embodiments, the present invention relates to any of the aforementioned methods, wherein the piece of porous plastic has an average length of about 0.4".

In certain embodiments, the present invention relates to any of the aforementioned methods, wherein the friable seal comprises plastic. In certain embodiments, the present invention relates to any of the aforementioned methods, wherein the friable seal comprises metal. In certain embodiments, the present invention relates to any of the aforementioned methods, wherein the exterior surface of the friable seal is coated with a wax or a plastic.

In certain embodiments, the present invention relates to any of the aforementioned methods, wherein the friable seal is at the distal end of the applicator body. In certain embodiments, the present invention relates to any of the aforementioned methods, wherein the friable seal is less than 0.1" from the distal end of the applicator body. In certain embodiments, the present invention relates to any of the aforementioned methods, wherein the friable seal is less than 0.25" from the distal end of the applicator body. In certain embodiments, the present invention relates to any of the aforementioned methods, wherein the friable seal is less than 0.50" from the distal end of the applicator body. In certain embodiments, the present invention relates to any of the aforementioned methods, wherein the friable seal is about 0.75" from the distal end of the applicator body.

In certain embodiments, the present invention relates to any of the aforementioned methods, further comprising the step of placing the tip on the distal end of the applicator body, wherein the tip is designed so as to break the friable seal when the distal end of the applicator body is connected to the proximal end of the tip.

Another aspect of the invention relates to a method of using an applicator to apply a hydrogel to a surface;

wherein the applicator comprises a tip and an applicator body; the tip comprises an open distal end, and an open proximal end; the applicator body comprises a proximal compartment comprising a mixture of a first liquid portion and a second liquid portion, a distal compartment comprising a solid portion, a closed proximal end, and an open distal end; wherein the proximal compartment and the distal compartment are separated by a first friable seal;

comprising the steps of:

breaking the first friable seal, causing the solid to come into contact with the mixture of the first liquid portion and the second liquid portion, thereby forming a liquid pre-hydrogel mixture;

applying the liquid pre-hydrogel mixture to a surface, wherein the pre-hydrogel mixture gels to form a hydrogel on the surface.

Another aspect of the invention relates to a method of using an applicator to apply a hydrogel to a surface;

wherein the applicator comprises a tip and an applicator body; the tip comprises an open distal end, and an open proximal end; the applicator body comprises a proximal compartment comprising a mixture of a first liquid portion and a second liquid portion, a distal compartment comprising a solid portion in a crushable ampoule, a closed proximal end, and an open distal end; wherein the proximal compartment and the distal compartment are separated by a first friable seal;

comprising the steps of:

breaking the first friable seal;

breaking the crushable ampoule, causing the solid to come into contact with the mixture of the first liquid portion and the second liquid portion, thereby forming a liquid pre-hydrogel mixture;

applying the liquid pre-hydrogel mixture to a surface, wherein the pre-hydrogel mixture gels to form a hydrogel on the surface.

Another aspect of the invention relates to a method of using an applicator to apply a hydrogel to a surface;

wherein the applicator comprises a tip and an applicator body; the tip comprises an open distal end, and an open proximal end; the applicator body comprises a proximal compartment comprising a first liquid portion, a middle compartment comprising a second liquid portion, a distal compartment comprising a solid portion in a crushable ampoule, a closed proximal end, and an open distal end; wherein the proximal compartment and the middle compartment are separated by a first friable seal; and the middle compartment and the distal compartment are separated by a second friable seal;

comprising the steps of:

breaking the first friable seal, causing the first liquid and the second liquid to mix;

breaking the second friable seal;

breaking the crushable ampoule, causing the solid to come into contact with the first liquid and the second liquid mixture, thereby forming a liquid pre-hydrogel mixture;

applying the liquid pre-hydrogel mixture to a surface, wherein the pre-hydrogel mixture gels to form a hydrogel on the surface.

In certain embodiments, the present invention relates to any of the aforementioned methods, wherein breaking the first friable seal comprises squeezing the applicator body at the point where the first friable seal resides.

In certain embodiments, the present invention relates to any of the aforementioned methods, wherein breaking the first friable seal comprises heating the applicator body at the point where the first friable seal resides.

In certain embodiments, the present invention relates to any of the aforementioned methods, wherein breaking the second friable seal comprises squeezing the applicator body at the point where the second friable seal resides.

In certain embodiments, the present invention relates to any of the aforementioned methods, wherein breaking the second friable seal comprises heating the applicator body at the point where the second friable seal resides.

In certain embodiments, the present invention relates to any of the aforementioned methods, wherein breaking the crushable ampoule comprises squeezing the applicator body wherein the crushable ampoule resides.

In certain embodiments, the present invention relates to any of the aforementioned methods, wherein the open proximal end of the tip is configured to attach to the open distal end of the applicator body.

In certain embodiments, the present invention relates to any of the aforementioned methods, wherein the open proximal end of the tip is attached to the open distal end of the applicator body.

In certain embodiments, the present invention relates to any of the aforementioned methods, further comprising a screen or filter placed in the tip.

In certain embodiments, the present invention relates to any of the aforementioned methods, further comprising a screen or filter placed between the open distal end of the applicator body and the open proximal end of the tip.

In certain embodiments, the present invention relates to any of the aforementioned methods, wherein the first liquid portion comprises a polyalkyleneimine, epoxy-resin component or polyurethane prepolymer. In certain embodiments, the present invention relates to any of the aforementioned methods, wherein the first liquid portion comprises a polyalkyleneimine. In certain embodiments, the present invention relates to any of the aforementioned methods, wherein the first liquid portion comprises PEI. In certain embodiments, the present invention relates to any of the aforementioned methods, wherein the second liquid portion comprises a buffer or curing agent. In certain embodiments, the present invention relates to any of the aforementioned methods, wherein the second liquid portion comprises a buffer.

In certain embodiments, the present invention relates to any of the aforementioned methods, wherein the solid comprises an activated PEG. In certain embodiments, the present invention relates to any of the aforementioned methods, wherein the solid comprises PEG-SPA or PEG-SG. In certain embodiments, the present invention relates to any of the aforementioned methods, wherein the solid comprises PEG-SG.

In certain embodiments, the present invention relates to any of the aforementioned methods, wherein the applicator body is tubular.

In certain embodiments, the present invention relates to any of the aforementioned methods, wherein the applicator body is made from a compressible material, wherein the compressible material permits manual pressurization. In certain embodiments, the present invention relates to any of the aforementioned methods, wherein the compressible material comprises plastic. In certain embodiments, the present invention relates to any of the aforementioned methods, wherein the compressible material comprises metal. In certain embodiments, the present invention relates to any of the aforementioned methods, wherein the compressible material is a laminate. In certain embodiments, the present invention relates to any of the aforementioned methods, wherein the compressible material is a glaminate.

In certain embodiments, the present invention relates to any of the aforementioned methods, wherein the length of the applicator body is between about 1" and about 9". In certain embodiments, the present invention relates to any of the aforementioned methods, wherein the length of the applicator body is about 9". In certain embodiments, the present invention relates to any of the aforementioned methods, wherein the length of the applicator body is about 8". In certain embodiments, the present invention relates to any of the aforementioned methods, wherein the length of the applicator body is about 7". In certain embodiments, the present invention relates to any of the aforementioned methods, wherein the length of the applicator body is about 6". In certain embodiments, the present invention relates to any of the aforementioned methods, wherein the length of the applicator body is about 5". In certain embodiments, the present invention relates to any of the aforementioned methods, wherein the length of the applicator body is about 4". In certain embodiments, the present invention relates to any of the aforementioned methods, wherein the length of the applicator body is about 3". In certain embodiments, the present invention relates to any of the aforementioned methods, wherein the length of the applicator body is about 2". In certain embodiments, the present invention relates to any of the aforementioned methods, wherein the length of the applicator body is about 1".

In certain embodiments, the present invention relates to any of the aforementioned methods, wherein the average outer diameter of the applicator body is between about 0.1" and about 2". In certain embodiments, the present invention relates to any of the aforementioned methods, wherein the average outer diameter of the applicator body is about 1.75". In certain embodiments, the present invention relates to any of the aforementioned methods, wherein the average outer diameter of the applicator body is about 1.50". In certain embodiments, the present invention relates to any of the aforementioned methods, wherein the average outer diameter of the applicator body is about 1.25". In certain embodiments, the present invention relates to any of the aforementioned methods, wherein the average outer diameter of the applicator body is about 1". In certain embodiments, the present invention relates to any of the aforementioned methods, wherein the average outer diameter of the applicator body is about 0.75". In certain embodiments, the present invention relates to any of the aforementioned methods, wherein the average outer diameter of the applicator body is about 0.5". In certain embodiments, the present invention relates to any of the aforementioned methods, wherein the average outer diameter of the applicator body is about 0.25".

In certain embodiments, the present invention relates to any of the aforementioned methods, wherein the average wall thickness of the applicator body is between about 0.001" and about 0.1". In certain embodiments, the present invention relates to any of the aforementioned methods, wherein the average wall thickness of the applicator body is between about 0.01" and about 0.03". In certain embodiments, the present invention relates to any of the aforementioned methods, wherein the average wall thickness of the applicator body is about 0.02".

In certain embodiments, the present invention relates to any of the aforementioned methods, wherein the tip is a nozzle tip. In certain embodiments, the present invention relates to any of the aforementioned methods, wherein the tip is a flow-thru brush.

In certain embodiments, the present invention relates to any of the aforementioned methods, wherein the tip further comprises a cannula, an inoculating loop, a brush, a sponge, a foam swab, a porous plastic component, a duck bill tip, a textile mitt or a spray tip affixed to the distal end of the tip. In certain embodiments, the present invention relates to any of the aforementioned methods, wherein the tip comprises a cannula. In certain embodiments, the present invention relates to any of the aforementioned methods, wherein the tip comprises an inoculating loop.

In certain embodiments, the present invention relates to any of the aforementioned methods, wherein the length of the tip is between about 0.1" and about 9.0". In certain embodiments, the present invention relates to any of the aforementioned methods, wherein the length of the tip is about 9.0". In certain embodiments, the present invention relates to any of the aforementioned methods, wherein the length of the tip is about 7.5". In certain embodiments, the present invention relates to any of the aforementioned methods, wherein the length of the tip is about 5.0". In certain embodiments, the present invention relates to any of the aforementioned methods, wherein the length of the tip is about 2.5". In certain embodiments, the present invention relates to any of the aforementioned methods, wherein the length of the tip is about 1.0". In certain embodiments, the present invention relates to any of the aforementioned methods, wherein the length of the tip is about 0.5".

In certain embodiments, the present invention relates to any of the aforementioned methods, wherein the diameter of the proximal end of the tip is between about 0.15" and about 0.55". In certain embodiments, the present invention relates to any of the aforementioned methods, wherein the diameter of the proximal end of the tip is about 0.35". In certain embodiments, the present invention relates to any of the aforementioned methods, wherein the diameter of the proximal end of the tip is about 0.25".

In certain embodiments, the present invention relates to any of the aforementioned methods, wherein the first friable seal comprises wax. In certain embodiments, the present invention relates to any of the aforementioned methods, wherein the second friable seal comprises wax. In certain embodiments, the present invention relates to any of the aforementioned methods, wherein the first friable seal comprises wax; and the second friable seal comprises wax. In certain embodiments, the present invention relates to any of the aforementioned methods, wherein the wax is beeswax, carnauba (a vegetable wax) or paraffin (a mineral wax).

In certain embodiments, the present invention relates to any of the aforementioned methods, wherein the first friable seal comprises wax and metal particles. In certain embodiments, the present invention relates to any of the aforementioned methods, wherein the first friable seal comprises wax and ferrous metal particles. In certain embodiments, the present invention relates to any of the aforementioned methods, wherein the second friable seal comprises wax and metal particles. In certain embodiments, the present invention relates to any of the aforementioned methods, wherein the second friable seal comprises wax and ferrous metal particles.

In certain embodiments, the present invention relates to any of the aforementioned methods, wherein the first friable seal consists essentially of wax. In certain embodiments, the present invention relates to any of the aforementioned methods, wherein the second friable seal consists essentially of wax. In certain embodiments, the present invention relates to any of the aforementioned methods, wherein the first friable seal consists essentially of wax; and the second friable seal consists essentially of wax. In certain embodiments, the present invention relates to any of the aforementioned methods, wherein the wax is beeswax, carnauba (a vegetable wax) or paraffin (a mineral wax).

In certain embodiments, the present invention relates to any of the aforementioned methods, wherein the first friable seal consists essentially of wax and metal particles. In certain embodiments, the present invention relates to any of the aforementioned methods, wherein the first friable seal consists essentially of wax and ferrous metal particles. In certain embodiments, the present invention relates to any of the aforementioned methods, wherein the second friable seal consists essentially of wax and metal particles. In certain embodiments, the present invention relates to any of the aforementioned methods, wherein the second friable seal consists essentially of wax and ferrous metal particles.

In certain embodiments, the present invention relates to any of the aforementioned methods, wherein both friable seals comprise plastic. In certain embodiments, the present invention relates to any of the aforementioned methods, wherein both friable seals comprises metal.

In certain embodiments, the present invention relates to any of the aforementioned methods, wherein the average thickness of the first friable seal is about 10 mm. In certain embodiments, the present invention relates to any of the aforementioned methods, wherein the average thickness of the first friable seal is about 7.5 mm. In certain embodiments, the present invention relates to any of the aforementioned methods, wherein the average thickness of the first friable seal is about 5 mm. In certain embodiments, the present invention relates to any of the aforementioned methods, wherein the average thickness of the first friable seal is about 2.5 mm. In certain embodiments, the present invention relates to any of the aforementioned methods, wherein the average thickness of the first friable seal is about 1 mm. In certain embodiments, the present invention relates to any of the aforementioned methods, wherein the average thickness of the second friable seal is about 10 mm. In certain embodiments, the present invention relates to any of the aforementioned methods, wherein the average thickness of the second friable seal is about 7.5 mm. In certain embodiments, the present invention relates to any of the aforementioned methods, wherein the average thickness of the second friable seal is about 5 mm. In certain embodiments, the present invention relates to any of the aforementioned methods, wherein the average thickness of the second friable seal is about 2.5 mm. In certain embodiments, the present invention relates to any of the aforementioned methods, wherein the average thickness of the second friable seal is about 1 mm.

In certain embodiments, the present invention relates to any of the aforementioned methods, wherein the first friable seal is about 1" from the proximal end of the applicator body. In certain embodiments, the present invention relates to any of the aforementioned methods, wherein the first friable seal is about 2" from the proximal end of the applicator body. In certain embodiments, the present invention relates to any of the aforementioned methods, wherein the first friable seal is about 3" from the proximal end of the applicator body. In certain embodiments, the present invention relates to any of the aforementioned methods, wherein the first friable seal is about 4" from the proximal end of the applicator body. In certain embodiments, the present invention relates to any of the aforementioned methods, wherein the first friable seal is about 5" from the proximal end of the applicator body. In certain embodiments, the present invention relates to any of the aforementioned methods, wherein the first friable seal is about 6" from the proximal end of the applicator body. In certain embodiments, the present invention relates to any of the aforementioned methods, wherein the first friable seal is about 7" from the proximal end of the applicator body. In certain embodiments, the present invention relates to any of the aforementioned methods, wherein the first friable seal is about 8" from the proximal end of the applicator body. In certain embodiments, the present invention relates to any of the aforementioned methods, wherein the first friable seal is about 9" from the proximal end of the applicator body.

In certain embodiments, the present invention relates to any of the aforementioned methods, wherein the second friable seal is about 1" from the distal end of the applicator body. In certain embodiments, the present invention relates to any of the aforementioned methods, wherein the second friable seal is about 2" from the distal end of the applicator body. In certain embodiments, the present invention relates to any of the aforementioned methods, wherein the second friable seal is about 3" from the distal end of the applicator body. In certain embodiments, the present invention relates to any of the aforementioned methods, wherein the second friable seal is about 4" from the distal end of the applicator body. In certain embodiments, the present invention relates to any of the aforementioned methods, wherein the second friable seal is about 5" from the distal end of the applicator body. In certain embodiments, the present invention relates to any of the aforementioned methods, wherein the second friable seal is about 6" from the distal end of the applicator body. In certain embodiments, the present invention relates to any of the aforementioned methods, wherein the second friable seal is about 7" from the distal end of the applicator body. In certain embodiments, the present invention relates to any of the aforementioned methods, wherein the second friable seal is about 8" from the distal end of the applicator body. In certain embodiments, the present invention relates to any of the aforementioned methods, wherein the second friable seal is about 9" from the distal end of the applicator body.

Another aspect of the invention relates to a method of using an applicator to apply a composition to a surface;
wherein the applicator comprises a handle, a brush and a solid; the brush is connected to one end of the handle; and the solid is adsorbed onto the brush;
comprising the step of:
using the applicator to apply the composition to the surface.

In certain embodiments, the present invention relates to any of the aforementioned methods, wherein the solid comprises an activated PEG. In certain embodiments, the present invention relates to any of the aforementioned methods, wherein the solid comprises PEG-SPA or PEG-SG. In certain embodiments, the present invention relates to any of the aforementioned methods, wherein the solid comprises PEG-SG.

Another aspect of the invention relates to a method of reconstituting an activated PEG, comprising the step of contacting a solid upon which an activated PEG has been adsorbed with a liquid.

In certain embodiments, the present invention relates to any of the aforementioned methods, wherein the solid is a piece of porous plastic. In certain embodiments, the present invention relates to any of the aforementioned methods, wherein the porous plastic is a polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a copolymer thereof. In certain embodiments, the present invention relates to any of the aforementioned methods, wherein the piece of porous plastic is a piece of polyester batting or other fibrous filter media material.

Another aspect of the invention relates to a method of using an applicator to apply a hydrogel to a surface;
wherein the applicator comprises an applicator body, a tip and a bladder; the applicator body comprises a storage receptacle for a liquid portion, a closed proximal end, an open distal end, and a friable seal or a removable separator separating the storage receptacle for the liquid portion from the open distal end; the tip comprises an open proximal end connected to the open distal end of the bladder, and an open distal end; the bladder comprises an open distal end that connects to the tip, and an open proximal end that connects to the applicator body;
comprising the steps of:
breaking the first friable seal, causing the solid to come into contact with the liquid portion, thereby forming a liquid pre-hydrogel mixture;
applying the liquid pre-hydrogel mixture to a surface, wherein the pre-hydrogel mixture gels to form a hydrogel on the surface.

In certain embodiments, the present invention relates to any of the aforementioned methods, wherein the applicator body is tubular. In certain embodiments, the present invention relates to any of the aforementioned methods, wherein the applicator body is a plastic ampoule.

In certain embodiments, the present invention relates to any of the aforementioned methods, wherein the applicator body further comprises a liquid in the storage receptacle for a liquid portion. In certain embodiments, the present invention relates to any of the aforementioned methods, wherein the liquid comprises a polyalkyleneimine. In certain embodiments, the present invention relates to any of the aforementioned methods, wherein the liquid comprises PEI.

In certain embodiments, the present invention relates to any of the aforementioned methods, wherein the applicator body is made from a compressible material, wherein the compressible material permits manual pressurization. In certain embodiments, the present invention relates to any of the aforementioned methods, wherein the compressible material comprises plastic. In certain embodiments, the present invention relates to any of the aforementioned methods, wherein the compressible material comprises metal. In certain embodiments, the present invention relates to any of the aforementioned methods, wherein the compressible material comprises paper. In certain embodiments, the present invention relates to any of the aforementioned methods, wherein the compressible material is a laminate. In certain embodiments, the present invention relates to any of the aforementioned methods, wherein the compressible material is a glaminate.

In certain embodiments, the present invention relates to any of the aforementioned methods, wherein the applicator body further comprises a springing mechanism in the interior of the applicator body, wherein the springing mechanism effects a spring back of the applicator body, thus facilitating the sucking back of components (e.g., the liquid portion and the solid portion) into the applicator body.

In certain embodiments, the present invention relates to any of the aforementioned methods, wherein the length of the applicator body is between about 1" and about 5". In certain embodiments, the present invention relates to any of the aforementioned methods, wherein the length of the applicator body is between about 2" and about 4". In certain embodiments, the present invention relates to any of the aforementioned methods, wherein the length of the applicator body is about 3". In certain embodiments, the present invention relates to any of the aforementioned methods, wherein the length of the applicator body is about 2". In certain embodiments, the present invention relates to any of the aforementioned methods, wherein the length of the applicator body is about 1".

In certain embodiments, the present invention relates to any of the aforementioned methods, wherein the average outer diameter of the applicator body is between about 0.15" and about 0.55". In certain embodiments, the present invention relates to any of the aforementioned methods, wherein the average outer diameter of the applicator body is about 0.35".

In certain embodiments, the present invention relates to any of the aforementioned methods, wherein the average wall thickness of the applicator body is between about 0.001" and about 0.1". In certain embodiments, the present invention relates to any of the aforementioned methods, wherein the average wall thickness of the applicator body is between about 0.01" and about 0.03". In certain embodiments, the present invention relates to any of the aforementioned methods, wherein the average wall thickness of the applicator body is about 0.02".

In certain embodiments, the present invention relates to any of the aforementioned methods, wherein the tip is a nozzle tip. In certain embodiments, the present invention relates to any of the aforementioned methods, wherein the tip is a nozzle tip.

In certain embodiments, the present invention relates to any of the aforementioned methods, wherein the tip further comprises a brush, a sponge, a foam swab, a porous plastic component, a duck bill tip, a textile mitt or a spray tip affixed to the distal end of the tip.

In certain embodiments, the present invention relates to any of the aforementioned methods, wherein the tip is a flow-thru brush.

In certain embodiments, the present invention relates to any of the aforementioned methods, wherein the bladder comprises a storage receptacle for a solid portion. In certain embodiments, the present invention relates to any of the aforementioned methods, wherein the bladder further comprises a solid in the storage receptacle for a solid portion. In certain embodiments, the present invention relates to any of the aforementioned methods, wherein the solid comprises an activated PEG. In certain embodiments, the present invention relates to any of the aforementioned methods, wherein the solid comprises PEG-SPA or PEG-SG. In certain embodiments, the present invention relates to any of the aforementioned methods, wherein the solid comprises PEG-SG.

In certain embodiments, the present invention relates to the aforementioned method, further comprising a solid; wherein the solid is located in the interior aspect of the bladder.

In certain embodiments, the present invention relates to any of the aforementioned methods, wherein the length of the tip is between about 0.1" and about 2.0". In certain embodiments, the present invention relates to any of the aforementioned methods, wherein the length of the tip is between about 0.6" and about 1.2". In certain embodiments, the present invention relates to any of the aforementioned methods, wherein the length of the tip is about 1.0". In certain embodiments, the present invention relates to any of the aforementioned methods, wherein the length of the tip is about 0.8".

In certain embodiments, the present invention relates to any of the aforementioned methods, wherein the diameter of the proximal end of the tip is between about 0.15" and about 0.55". In certain embodiments, the present invention relates to any of the aforementioned methods, wherein the diameter of the proximal end of the tip is about 0.35". In certain embodiments, the present invention relates to any of the aforementioned methods, wherein the diameter of the proximal end of the tip is about 0.25".

In certain embodiments, the present invention relates to any of the aforementioned methods, further comprising a solid; wherein the solid is adsorbed onto the interior walls of the bladder. In certain embodiments, the present invention relates to any of the aforementioned methods, wherein the solid adsorbed onto the interior walls of the bladder comprises an activated PEG. In certain embodiments, the present invention relates to any of the aforementioned methods, wherein the solid adsorbed onto the interior walls of the bladder comprises PEG-SPA or PEG-SG. In certain embodiments, the present invention relates to any of the aforementioned methods, wherein the solid adsorbed onto the interior walls of the bladder comprises PEG-SPA.

In certain embodiments, the present invention relates to any of the aforementioned methods, wherein the storage receptacle for a solid portion comprises a piece of porous plastic upon which a solid has been adsorbed. In certain embodiments, the present invention relates to any of the aforementioned methods, wherein the solid adsorbed onto the piece of porous plastic comprises an activated PEG. In certain embodiments, the present invention relates to any of the aforementioned methods, wherein the solid adsorbed onto the piece of porous plastic comprises PEG-SPA or PEG-SG. In certain embodiments, the present invention relates to any of the aforementioned methods, wherein the solid adsorbed onto the piece of porous plastic comprises PEG-SPA.

In certain embodiments, the present invention relates to the aforementioned application, wherein the piece of porous plastic is a piece of polyethylene (PE), polypropylene (PP), high-density polyethylene (HDPE), ultra-high molecular weight polyethylene (UHMWPE), polytetrafluoroethylene (PTFE), nylon, polyvinylidine fluoride (PVDF), polyethersulfone (PES), ethyl vinyl acetate (EVA), or a co-polymer thereof. In certain embodiments, the present invention relates to any of the aforementioned methods, wherein the piece of porous plastic is a piece of polyester batting or other fibrous filter media material.

In certain embodiments, the present invention relates to any of the aforementioned methods, wherein the piece of porous plastic has an average diameter between about 0.02" and about 0.32". In certain embodiments, the present invention relates to any of the aforementioned methods, wherein the piece of porous plastic has an average diameter between about 0.12" and about 0.22". In certain embodiments, the present invention relates to any of the aforementioned methods, wherein the piece of porous plastic has an average diameter of about 0.17".

In certain embodiments, the present invention relates to any of the aforementioned methods, wherein the piece of porous plastic has an average length of between about 0.2" and about 0.6". In certain embodiments, the present invention relates to any of the aforementioned methods, wherein the piece of porous plastic has an average length of between about 0.3" and about 0.5". In certain embodiments, the present invention relates to any of the aforementioned methods, wherein the piece of porous plastic has an average length of about 0.4".

In certain embodiments, the present invention relates to any of the aforementioned methods, wherein the applicator body comprises a friable seal.

In certain embodiments, the present invention relates to any of the aforementioned methods, wherein the friable seal comprises plastic. In certain embodiments, the present invention relates to any of the aforementioned methods, wherein the friable seal comprises metal. In certain embodiments, the present invention relates to any of the aforementioned methods, wherein the exterior surface of the friable seal is coated with a wax or a plastic.

In certain embodiments, the present invention relates to any of the aforementioned methods, wherein the friable seal is at the distal end of the applicator body. In certain embodiments, the present invention relates to any of the aforementioned methods, wherein the friable seal is less than 0.1" from the distal end of the applicator body. In certain embodiments, the present invention relates to any of the aforementioned methods, wherein the friable seal is less than 0.25" from the distal end of the applicator body. In certain embodiments, the present invention relates to any of the aforementioned methods, wherein the friable seal is less than 0.50" from the distal end of the applicator body. In certain embodiments, the present invention relates to any of the aforementioned methods, wherein the friable seal is about 0.75" from the distal end of the applicator body.

In certain embodiments, the present invention relates to any of the aforementioned methods, wherein the friable seal comprises wax. In certain embodiments, the present invention relates to any of the aforementioned methods, wherein the wax is beeswax, carnauba (a vegetable wax) or paraffin (a mineral wax).

In certain embodiments, the present invention relates to any of the aforementioned methods, wherein the friable seal comprises wax and metal particles. In certain embodiments, the present invention relates to any of the aforementioned methods, wherein the friable seal comprises wax and ferrous metal particles.

In certain embodiments, the present invention relates to any of the aforementioned methods, wherein the friable seal consists essentially of wax. In certain embodiments, the present invention relates to any of the aforementioned methods, wherein the wax is beeswax, carnauba (a vegetable wax) or paraffin (a mineral wax).

In certain embodiments, the present invention relates to any of the aforementioned methods, wherein the average thickness of the friable seal is about 10 mm. In certain embodiments, the present invention relates to any of the aforementioned methods, wherein the average thickness of the friable seal is about 7.5 mm. In certain embodiments, the present invention relates to any of the aforementioned methods, wherein the average thickness of the friable seal is about 5 mm. In certain embodiments, the present invention relates to any of the aforementioned methods, wherein the average thickness of the friable seal is about 2.5 mm. In certain embodiments, the present invention relates to any of the aforementioned methods, wherein the average thickness of the friable seal is about 1 mm.

In certain embodiments, the present invention relates to any of the aforementioned methods, wherein the applicator body comprises a removable separator.

In certain embodiments, the present invention relates to any of the aforementioned methods, wherein the applicator further comprises a cap which engages the proximal end of the tip; and further comprises a solid receptacle.

Sterilization Procedures

A variety of procedures the applicators and/or the chemical composition contained therein. Sterilization may be accomplished by chemical, physical, or irradiation techniques. Examples of chemical methods include exposure to ethylene oxide or hydrogen peroxide vapor. Examples of physical methods include sterilization by heat (dry or moist), retort canning, and filtration. The British Pharmacopoeia recommends heating at a minimum of 160° C. for not less than 2 hours, a minimum of 170° C. for not less than 1 hour and a minimum of 180° C. for not less than 30 minutes for effective sterilization. For examples of heat sterilization, see U.S. Pat. No. 6,136,326, which is hereby incorporated by reference. Passing the chemical composition through a membrane can be used to sterilize a composition. For example, the composition is filtered through a small pore filter such as a 0.22 micron filter which comprises material inert to the composition being filtered. In certain instances, the filtration is conducted in a Class 100,000 or better clean room. Examples of irradiation methods include gamma irradiation, electron beam irradiation, microwave irradiation, and irradiation using visible light. One preferred method is electron beam irradiation, as described in U.S. Pat. Nos. 6,743,858; 6,248,800; and 6,143,805, each of which is hereby incorporated by reference.

There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "canned" beam, prior to leaving the vacuum enclosure through a beam window. The dose can be adjusted with the control of the percent scan, the beam current, and the conveyor speed. In certain instances, the electron-beam radiation employed may be maintained at an initial fluence of at least about 2 µCurie/cm$^2$, at least about 5 µCurie/cm$^2$, at least about 8 µCurie/cm$^2$, or at least about 10 µCurie/cm$^2$. In certain instances, the electron-beam radiation employed has an initial fluence of from about 2 to about 25 µCurie/cm$^2$. In certain instances, the electron-beam dosage is from about 5 to 50 kGray, or from about 15 to about 20 kGray with the specific dosage being selected relative to the density of material being subjected to electron-beam radiation as well as the amount of bioburden estimated to be therein. Such factors are well within the skill of the art.

The applicators and/or composition to be sterilized may be in any type of at least partially electron beam permeable container such as glass or plastic. In embodiments of the present invention, the container may be sealed or have an opening. Examples of glass containers include ampules, vials, syringes, pipettes, applicators, and the like. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

Procedures for sterilization using visible light are described in U.S. Pat. No. 6,579,916, which is hereby incorporated by reference. The visible light for sterilization can be generated using any conventional generator of sufficient power and breadth of wavelength to effect sterilization. Generators are commercially available under the tradename PureBright® in-line sterilization systems from PurePulse Technologies, Inc. 4241 Ponderosa Ave, San Diego, Calif. 92123, USA. The PureBright® in-line sterilization system employs visible light to sterilize clear liquids at an intensity approximately 90000 times greater than surface sunlight. If the amount of UV light penetration is of concern, conventional UV absorbing materials can be used to filter out the UV light.

In a preferred embodiment, the composition in the applicator is sterilized to provide a Sterility Assurance Level (SAL) of at least about $10^{-3}$. The Sterility Assurance Level measurement standard is described, for example, in ISO/CD 14937, the entire disclosure of which is incorporated herein by reference. In certain embodiments, the Sterility Assurance Level may be at least about $10^{-4}$, at least about $10^{-5}$, or at least about $10^{-6}$.

As discussed above, in certain embodiments of the present invention, one or more of the compositions, reagents, or components of a kit has been sterilized. The sterilization may be achieved using gamma radiation, e-beam radiation, dry heat sterilization, ethylene oxide sterilization, or a combination of any of them. The compositions, reagents, or components of the kits can be sterilized in an aqueous solution or neat.

In certain embodiments a compound present in an applicator (as described herein) has been sterilized by e-beam radiation between 2-40 kGy; or between 3-20 kGy; or between 5-12 kGy.

In certain embodiments, said sterilization is carried out below 30° C. In certain embodiments, said sterilization is carried out below 20° C. In certain embodiments, said sterilization is carried out below 10° C. In certain embodiments, said sterilization is carried out below 0° C.

Kits

In another aspect of the invention kits are provided containing one or more applicators of the invention. A "kit," as used herein, typically defines a package or an assembly including one or more of the applicators of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, modifying, assembling, storing, packaging, preparing, mixing, diluting, and/or preserving the compositions components for a particular use.

A kit of the invention may include instructions in any form that are provided in connection with the applicators of the invention in such a manner that one of ordinary skill in the art would recognize that the instructions are to be associated with the compositions of the invention. For instance, the instructions may relate to the use, modification, mixing, diluting, preserving, assembly, storage, packaging, and/or preparation of the applicators and/or other compositions associated with the kit. In some cases, the instructions may also include instructions for the use of the applicators. The instructions may be provided in any form recognizable by a user as a suitable vehicle for containing such instructions; for example, written or published, verbal, audible (e.g., telephonic), digital, optical, visual (e.g., videotape, DVD, etc.) or electronic communications (including Internet or web-based communications), provided in any manner.

In certain embodiments, different parts of the applicators may be packaged separately (e.g. in Mylar pouches). For example, in some circumstances it may be advantageous to package the solid containing components and liquid containing components separately.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, an "applicator body" is a container which is constructed to hold multiple components (such a solids and liquids). As is described herein, certain applicator bodies of the invention are designed to be connected with a solid-containing "tip," thereby facilitating the mixing of the components contained in the applicator body. In other embodiments, solid-containing "caps" cover the open end of a tip. The tips and caps of the invention are described in further detail herein.

As used herein, a "storage receptacle" may be a container, such as an ampoule, but may alternatively be a space or are defined within an applicator body, bladder, tip or cap, which can hold a solid or a liquid. For example, if the proximal end of an applicator body is closed, and a friable seal is placed somewhere along the length of the applicator body, a space is defined between the proximal end of the applicator body and the friable seal which can be a storage receptacle for, for example, a liquid.

The term "glaminate tube" is known to those skilled in the art and refers to tubes formed from laminated layers of plastic, metal and paper. For example, toothpaste is often sold in glaminate tubes.

The term "nozzle" as used herein is known to those skilled in the art and refers to a mechanical device designed to control the characteristics of a fluid flow as it exits from an enclosed chamber (such as an applicator body) into some medium. A nozzle is often a tube of varying diameter, and it can be used to direct or modify the flow of a liquid or gas. Nozzles are frequently used to control the rate of flow, speed, direction, and/or the pressure of the stream that emerges from them. In certain embodiments the proximal end of a nozzle, wherein the fluid flow enters, will have a larger diameter than the distal end of a nozzle, where the fluid flow exists. This is known as a convergent nozzle (i.e., narrowing down from a wide diameter to a smaller diameter in the direction of the flow). In other embodiments the nozzle can be characterized as divergent (i.e., expanding from a smaller diameter to a larger one).

The term "brush" or "brush cannula" as used herein is known to those skilled in the art. The name represents the function of the brush: It is constructed to enable liquid to flow through the bristles for an application. The brushes can be attached to a wide variety of media that dispense liquid, and can be made out of many types of bristle material and configurations. In certain embodiments herein the brush cannula is connected to an applicator body. Brush cannulas are also known as flow-thru brushes; the terms are used interchangeably herein.

The term "activated PEG" as used herein is known to those skilled in the art and refers to poly(ethylene) glycols which typically have either both ends activated for conjugation with other molecules, or have one end capped as an ether (e.g., a methyl ether) and the other end activated for conjugation with another molecule. Shown below are chemical structures for polyethylene glycol (PEG), mono-methylated polyethylene glycol (mPEG), and an activated mPEG.

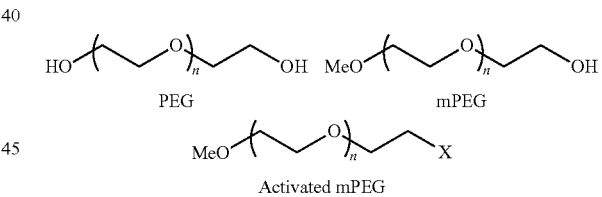

In the structures provided above n is a positive integer. In a batch of activated PEG different individual molecules will have different values of n (i.e., the mixture is polydisperse); these mixtures are often characterized by an average molecular weight, which can be converted into an average value for n. In certain embodiments herein, the average n is between about 50 and about 200. In other embodiments the average n is between about 80 and about 120. In yet other embodiments, the average n is about 100. In addition, in the structures provided above, X can be a variety of chemical moieties such as, for example, a N-succinimide, N-maleimide, a nitro, an aldehyde, an amine, a thiol, a ketal, an acetal, or a carbonate. In certain embodiments, X is selected from the group consisting of —$CH_2C(=O)O$(N-succinimidyl), —$C(=O)CH_2CH_2C(=O)O$(N-succinimidyl), —$C(=O)CH_2CH_2CH_2C(=O)O$(N-succinimidyl), —$CH_2CH_2CH_2CH_2CH_2C(=O)O$(N-succinimidyl), —$C(=O)$(p-nitrophenyl), —$CH_2CH_2C(=O)H$, —$CH_2CH_2CH_2NH_2$, —$CH_2CH_2CH(OCH_2CH_3)_2$, —CH$_2$CH$_2$SH, —CH$_2$CH$_2$CH$_2$N(H)C(=O)CH$_2$CH$_2$(N-maleimidyl), and —O(C=O)O(p-nitrophenyl).

As used herein, "wax" refers to a substance with properties similar to beeswax, namely that it is plastic (malleable) at normal ambient temperatures; it has a melting point above approximately 45° C. (113° F.) (which differentiates waxes from fats and oils); it has a relatively low viscosity when melted (unlike many plastics); and it is hydrophobic. Waxes may be natural or artificial. In addition to beeswax, carnauba (a vegetable wax) and paraffin (a mineral wax) are commonly encountered waxes which occur naturally. Chemically, a wax may be, for example, an ester of ethylene glycol (ethan-1,2-diol) and two fatty acids. It may also be a combination of other fatty alcohols with fatty acids. In addition to the waxes listed above, non-limiting examples of waxes of the invention include chinese wax (produced by scale insects *Coccus ceriferus*), shellac wax (from the lac insect *Coccus lacca*), spermaceti (from the head cavities and blubber of the Sperm Whale), lanolin (or wool wax, from the sebaceous glands of sheep), bayberry wax (from the surface of the berries of the bayberry shrub), candelilla wax (from the Mexican shrubs *Euphorbia cerifera* and *E. antisyphilitica*), carnauba wax (from the leaves of the Carnauba Palm), castor wax (catalytically hydrogenated castor oil), esparto wax (a byproduct of making paper from esparto grass), jojoba oil (pressed from the seeds of the jojoba bush), ouricury wax (from the Brazilian Feather Palm), rice bran wax (obtained from rice bran), ceresin waxes, montan wax (extracted from lignite and brown coal), ozocerite (found in lignite beds), peat waxes, petroleum waxes (such as paraffin wax which is made of long-chain alkane hydrocarbons), polyethylene waxes (based on polyethylene), Fischer-Tropsch waxes, substituted amide waxes, and polymerized α-olefins, as well as any of the above waxes which have been chemically modified (for example esterified or saponified).

As used herein, an "ampoule" is a small vial which is hermetically sealed after filling. An ampoule of the invention is designed so that it will rupture when it is squeezed (e.g., by hand). In certain embodiments, an ampoule is made out of glass, but any material which ruptures when squeezed may be used.

As used herein, a "seal" is synonymous with a membrane or a barrier which serves as a means by which two components are separated by each other.

As used here, a seal which is "friable" is one which is capable of being broken, melted, crumbled, pulverized, or reduced to powder by hand pressure or heat.

As used herein "plastic" refers to polyacrylics, polyolefins, polystyrenes, polyesters, polyethers, polyurethanes, polycarbonates, polyamines, or co-polymers thereof.

As used herein, the term "patient" refers to any animal in need, including primates, in particular humans, and other mammals such as equines, cattle, swine and sheep; and poultry and pets in general.

EXEMPLIFICATION

The invention now being generally described, it will be more readily understood by reference to the following examples, which are included merely for purposes of illustration of certain aspects and embodiments of the present invention, and are not intended to limit the invention.

Example 1

A nozzle tip was filled with a 0.072 mL aliquot of a solution made from 2 grams of 3400 molecular weight PEG-SPA (propionic acid succinimidyl ester of polyethylene glycol) in 4 mL of anhydrous acetone (0.5 g/mL) and allowed to dry. A 0.223 mL aliquot of PEI buffer (polyethyleneimine buffer) solution was placed into a JAC plastic amp. The impregnated tip was placed onto the JAC plastic amp and manually pressurized while the tip was placed over a weighing pan. The resulting solution was allowed to flow back through the applicator by reducing the manual compression force on tubular body. The pressurization and release (suck back) was repeated 2 additional times and the resulting solution was expressed out onto a weighing pan. The resulting solution gelled in approximately 30 seconds.

Example 2

A nozzle tip was fitted with a piece of porous plastic (Porex Porous Plastics) of approximately 0.25" diameter and 0.45" in length. The location of the porous plastic piece was in the most proximal end of the nozzle tip. The porous plastic piece was impregnated with a 0.072 mL aliquot of a solution made from 2 grams of 3400 molecular weight PEG-SPA in 4 mL of anhydrous acetone (0.5 g/mL) and allowed to dry. A 0.223 mL aliquot of PEI buffer solution was placed into a JAC plastic amp. The impregnated tip was placed onto the JAC plastic amp and manually pressurized while the tip was placed over a weighing pan. The resulting solution was allowed to flow back through the applicator by reducing the manual compression force on the tubular body. The pressurization and release (suck back) was repeated 2 additional times and the resulting solution was expressed out onto a weighing pan. The resulting solution gelled in approximately 30 seconds.

Example 3

An flow-thru brush was fitted with a piece of polymeric tubing to allow it to be mated into the open end of a JAC plastic amp and a piece of Poly-fil* polyester batting or other fibrous filter media material. The batting material was then impregnated with 0.072 mL of a 0.5 g/mL 3400 PEG-SPA in anhydrous acetone and allowed to dry. This impregnated brush applicator tip was then mated with a JAC plastic amp with 0.225 mL of PEI buffer solution. The plastic amp was then manually pressurized while the tip was placed over a weighing pan. The resulting solution was allowed to flow back through the applicator by reducing the manual compression force on the tubular body. The pressurization and release (suck back) was repeated several additional times and the resulting solution was expressed out onto a weighing pan. The resulting solution gelled in approximately 30 seconds.

Example 4

An flow-thru brush was fitted with a piece of polymeric tubing to allow it to be mated into the open end of a JAC plastic amp and a piece of porous plastic material. The porous plastic material was approximately 0.25" in diameter and 0.4" long and was located within the polymeric tubing, directly behind the flow-thru brush tip. The porous plastic material was then impregnated with 0.072 mL of a 0.5 g/mL 3400 PEG-SPA in anhydrous acetone and allowed to dry. This impregnated brush applicator tip was then mated with a JAC plastic amp with 0.225 mL of PEI buffer solution. The plastic amp was then manually pressurized while the tip was placed over a weighing pan. The resulting solution was allowed to flow back through the applicator by reducing the manual compression force on the tubular body. The pressurization and release (suck back) was repeated several additional times and the resulting solution was expressed out onto a weighing pan. The resulting solution gelled in approximately 30 seconds.

Example 5

An flow-thru brush was fitted with a piece of polymeric tubing to allow it to be mated into the open end of a JAC plastic amp and a piece of porous polyurethane foam. The foam material was then impregnated with 0.072 mL of a 0.5 g/mL 3400 PEG-SPA in anhydrous acetone and allowed to dry. This impregnated brush applicator tip was then mated with a JAC plastic amp with 0.225 mL of PEI buffer solution. The plastic amp was then manually pressurized while the tip was placed over a weighing pan. The resulting solution was allowed to flow back through the applicator by reducing the manual compression force on the tubular body. The pressurization and release (suck back) was repeated several additional times and the resulting solution was expressed out onto a weighing pan. The resulting solution gelled in approximately 30 seconds.

Example 6

An flow-thru brush was fitted with a piece of polymeric tubing to allow it to be mated into the open end of a JAC plastic amp and a piece of porous plastic. The porous plastic was approximately 0.17" in diameter and 0.35" long and was located in the interior cavity of the proximal aspect of the flow-thru brush tip. The porous plastic material was then impregnated with 0.072 mL of a 0.5 g/mL 3400 PEG-SPA in anhydrous acetone and allowed to dry. This impregnated brush applicator tip was then mated with a JAC plastic amp with 0.225 mL of PEI buffer solution. The plastic amp was then manually pressurized while the tip was placed over a weighing pan. The resulting solution was allowed to flow back through the applicator by reducing the manual compression force on the tubular body. The pressurization and release (suck back) was repeated several additional times and the resulting solution was expressed out onto a weighing pan. The resulting solution gelled in approximately 30 seconds.

Example 7

An flow-thru brush was fitted with a piece of polymeric tubing to allow it to be mated into the open end of a JAC plastic amp and a piece of porous plastic impregnated with PEG as described in Example 6. A cap designed to fit onto the distal end of the flow-thru brush applicator was placed onto the brush tip. This impregnated brush applicator tip was then mated with a JAC plastic amp with 0.225 mL of PEI buffer solution. The plastic amp was then manually pressurized. The resulting solution flowed through the flow-thru brush tip and into the space between the exterior of the flow-thru brush and the interior aspect of the cap. The resulting solution was allowed to flow back through the applicator by reducing the manual compression force on tubular body. The pressurization and release (suck back) was repeated several additional times and the solution was allowed to remain momentarily within the plastic amp. The cap was removed and the solution was expressed into a weighing pan. The resulting solution gelled in approximately 30 seconds.

Example 8

A PEG impregnated flow-thru brush applicator tip with attached cap of working example 7 is placed within a separate Mylar® foil pouch (moisture and oxygen barrier). The PEI buffer solution filled JAC Plastic Amp is placed within a second, separate Mylar® foil pouch. Just prior to use, the physician or nursing staff removes the impregnated brush tip and the filled JAC Plastic Amp from their respective Mylar® foil pouches and fits the brush tip into the JAC plastic Amp. At time of use, the friable seal is ruptured by manual pressure, the liquid and powder portions of the formulation are mixed by alternatingly applying manual pressure and relieving the pressure several times. The cap is then removed from the brush tip and the liquid formulation is applied to the tissue surface. The resulting liquid should gel in approximately 20 seconds.

Example 9

A PEG impregnated flow-thru brush applicator tip similar to that described in working example 6 is produced with a piercing feature on the most proximal aspect of the tip shank. An aluminum ointment tube is filled with PEI buffer solution and sealed. The aluminum tube and impregnated brush tip are assembled such that the brush tip is on the distal aspect of the aluminum tube, but the piercing feature does not engage the aluminum tube. The assembled device is placed into a single, Mylar® foil pouch and sealed. At time of use, the nurse or physician removes the device from the Mylar® foil pouch, manually engages the piercing feature of the brush tip and squeezes the aluminum tube, thus mixing the liquid buffer with the powdered PEG-SPA. Further manual pressurization expels the formulation onto the surface of the tissue to be treated and the resulting liquid should gels in approximately 20 seconds.

Example 10

A PEG-SPA impregnated flow-thru brush applicator tip with cap similar to that described in working example 7 is produced with a piercing feature on the most proximal aspect of the tip shank. An aluminum ointment tube is fitted with an internal springback mechanism and filled with PEI buffer solution and then sealed. The aluminum tube and impregnated brush tip are assembled such that the brush tip is on the distal aspect of the aluminum tube, but the piercing feature does not engage the aluminum tube. The assembled device is placed into a single, Mylar® foil pouch and sealed. At time of use, the nurse or physician removes the device from the Mylar® foil pouch, manually engages the piercing feature of the brush tip and squeezes the aluminum tube forcing the liquid into the powdered PEG, out through the flow-thru brush and into the space between the cap and brush tip. The user then partially releases manual pressure which allows the internal springback mechanism to force the aluminum tube to open slightly, causing the solution to be drawn back into the aluminum tube. The formulation is mixed by alternatingly applying manual pressure and relieving the pressure several times. The cap is then removed and the formulation is applied to the intended tissue. The resulting liquid formulation should gel in approximately 20 seconds.

Example 11

An PEG-SG containing applicator of FIG. 2A was produced using 0.6 mL of buffered PEI solution in a 6.7 mm diameter by 35 mm long onion skin glass ampoule. 45 mg of PEG-SG was added to the bottom of a 6 cc LDPE bottle (US Plastic #66524), the filled glass ampoule was placed into the bottle and a flow through brush with a porous plastic filter was placed into the mouth of the bottle. The unit was activated by manually squeezing the bottle until the glass ampoule broke and then shaking the contents vigorously to mix the components. The bottle was then inverted and squeezed to liberate the mixed, liquid hydrogel formulation. The hydrogel solidified in approximately 40 seconds.

Example 12

Applicators of the design of FIG. 3A in which a 8.9 mm OD (8 mm ID) by 82 mm long tube (JAC #F011J) was utilized to house a 35 mm long glass ampoule holding 0.65 mL of buffer solution and a second glass ampoule containing 0.10 mL of concentrated PEI solution. In addition, 50 mg of PEG-SG was added to the interior aspect of the tube along with the sealed ampoules. To the open end of the polymeric tube, a flow through brush with porous plastic filter element was affixed. The device was activated by first breaking the buffer containing ampoule and shaking vigorously to mix the PEG-SG into the buffer solution Then the PEI containing ampoule was broken and the device was again shaken to mix the components. The resulting liquid hydrogel formulation solidified in about 40 seconds.

Example 13

Applicators of the design of FIG. 3B were made with the same components as mentioned in example 2 with the addition of a pvc plastisol bladder and screen. To the open end distal of the pvc plastisol bladder, a flow through brush with porous plastic filter element was affixed. The device was activated by first breaking the buffer containing ampoule and shaking vigorously to mix the PEG-SG into the buffer solution Then the PEI containing ampoule was broken and the device was again shaken to mix the components. A gentle squeeze of the bladder resulted in the liquid formulation being easily expressed out of the applicator. The resulting liquid hydrogel formulation solidified in about 40 seconds.

Example 14

Figure 4:
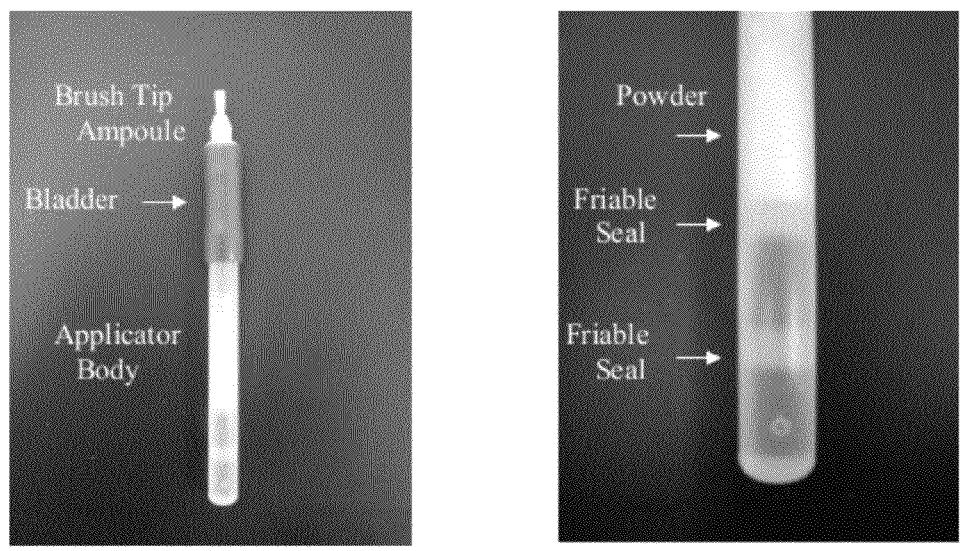
FIG. 4 depicts an applicator which houses two liquids in separate chambers, separated by friable seals, and a solid in a glass ampoule.

Applicators of FIG. 4 were made using a tubular applicator with 8.9 mm OD (8 mm ID) by 82 mm long tube (JAC #F011J) by 8 mm ID. To this, 0.6 mL of PEI solution was placed into the bottom of the tube. This was followed by approximately 100 mg of refine paraffin wax. The filled tube was placed into a convection oven set at 85° C. for 30 minutes. This caused the wax to melt and liquefy. The tube was removed from the oven and allowed to air cool, solidifying the wax on the upper surface of the PEI solution. 0.6 mL of buffer solution was placed on top of the first wax seal with a second 100 mg of wax and the tube was placed into a plastic chromatography vial rack with the second wax material slightly above the height of the top surface of the rack. A heat gun was used to melt the second wax without disrupting the first wax seal. (The wax seals had an exaggerated meniscus of approximately 5.5 mm on the interior aspect of the tube) Once the second wax seal solidified, an ampoule containing 0.100 gram of PEG-SG was placed on top of the second wax seal. A screen, a bladder and a flow through tip were all added. The device was actuated by first disrupting the first seal, then disrupting the second seal and lastly breaking the PEG-SG containing ampoule. The device was again shaken to mix the components. A gentle squeeze of the bladder resulted in the liquid formulation being easily expressed out of the applicator. The resulting liquid hydrogel formulation solidified in about 40 seconds.

Example 15

Figure 6:
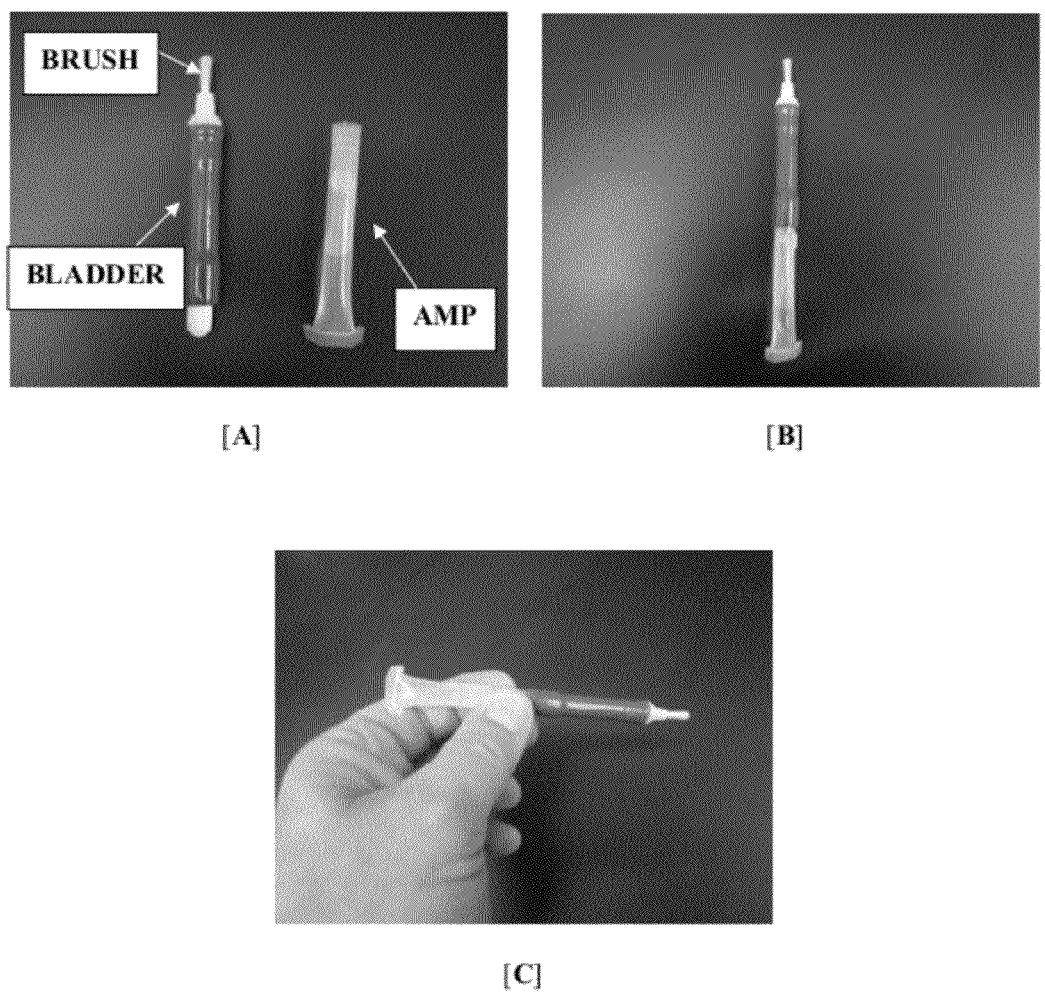
FIG. 6 depicts a two component applicator of the invention, wherein one component comprises the brush.

An Andon flow through brush was mated to a PVC plastisol bladder. Into the bladder was placed 0.2 grams of activated PEG. A cap was placed into the open end of the bladder. This was packaged into a foil Mylar® pouch. Separately, a JAC plastic amp was filled with 1.2 mL of mixed PEI/buffer solution. At time of use, the white cap was removed, and the JAC plastic Amp filled with a mixed solution of buffer and PEI was fitted to the Andon flow through brush/bladder assembly. With the tip pointing downward, the plastic amp was squeezed to break the internal septum, the applicator body was squeezed several times in order to convey the liquid into the bladder area of the device. The device was then shaken rigorously to mix the ingredients and applied to the intended surface whereupon it solidified in approximately 30 seconds. See, for example, FIG. 6.

Example 16

An Andon flow through brush was fitted with a filter in the internal fluid pathway. The filter/brush tip was then placed into one end of a PVC plastisol bladder. A closed end polymeric tube was filled with 1.2 mL of a mixed PEI/buffer solution and 95 mg of fully refined paraffin wax was placed into the filled tube. The tube was subjected to a 90 minute heat cycle in a vacuum oven set to 120° C. and cycled three times between −15 inches Hg to −5 inches Hg with an argon backfill. After three cycles was completed, the remainder of the heat cycle was accomplished at −5 inches of Hg. The tube was then placed into a 50° C. gravity feed convection oven for a controlled cool-down of 90 additional minutes. Once completed, the tube was fitted with an ampoule containing 200 mg of activated PEG which was sealed under argon back fill. The ampoule containing filled tube was then fitted with the brush tip/bladder/cap/filter assembly and sealed within an argon filled foil Mylar® pouch. The device was then sterilized by radiation. The sterile device was then removed from its packaging and the tube was squeezed to disrupt the wax seal, thus liberating the liquid. The tube was further squeezed to break the glass ampoule and liberate the activated PEG. The applicator was then shaken to mix the components and the formulation was expressed through the brush tip whereupon it gelled in approximately 30 seconds.

INCORPORATION BY REFERENCE

All of the U.S. patents and U.S. published patent applications cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A kit comprising an applicator body and a brush/bladder assembly;
wherein
the applicator body comprises a storage receptacle for a liquid portion, a closed proximal end, an open distal end, and a first friable seal or a removable separator separating the storage receptacle for the liquid portion from the open distal end, the storage receptacle for the liquid portion comprising a buffered solution of polyethyleneimine (PEI);
the brush/bladder assembly comprises a flow-thru brush tip, a cap and a bladder;
the tip comprises an open proximal end and an open distal end;
the cap fits snugly onto the exterior surface of the flow-thru brush tip;
the bladder comprises an open distal end connected to the open proximal end of the tip, an open proximal end configured to attach to the open distal end of the applicator body, and a powdered activated poly(ethylene) glycol (PEG); and
the powdered activated PEG activated ends.

2. The kit of claim 1, wherein the applicator body and the brush/bladder assembly are placed in separate foil bags or separate cavities within a single foil pouch.

3. An applicator, comprising an applicator body, a tip, and a bladder;
wherein
the applicator body comprises a storage receptacle for a liquid portion, a closed proximal end, an open distal end, and a friable seal or a removable separator separating the storage receptacle for the liquid portion from the open distal end, the storage receptacle for the liquid portion comprising a buffered solution of polyethyleneimine (PEI);
the tip is a flow-thru brush comprising an open proximal end and an open distal end;
the bladder comprises an open proximal end connected to the open distal end of the applicator body, an open distal end connected to the open proximal end of the tip, and an powdered activated poly(ethylene) glycol (PEG); and
the powdered activated PEG has activated ends.

* * * * *

UNITED STATES PATENT AND TRADEMARK OFFICE
CERTIFICATE OF CORRECTION

| | | |
|---|---|---|
| PATENT NO. | : 8,262,608 B2 | Page 1 of 1 |
| APPLICATION NO. | : 12/019996 | |
| DATED | : September 11, 2012 | |
| INVENTOR(S) | : Jeffrey G. Clark et al. | |

It is certified that error appears in the above-identified patent and that said Letters Patent is hereby corrected as shown below:

In the Claims:

At column 48, claim number 1, line number 6, replace:

"the powdered activated PEG activated ends."

with

-- the powdered activated PEG has activated ends. --

At column 48, claim number 3, line numbers 24-25, replace:

"and an powdered activated poly(ethylene) glycol (PEG);"

with

-- and a powdered activated poly(ethylene) glycol (PEG); --

Signed and Sealed this
Twentieth Day of November, 2012

David J. Kappos
*Director of the United States Patent and Trademark Office*